(12) United States Patent
Lapina et al.

(10) Patent No.: US 8,871,283 B2
(45) Date of Patent: Oct. 28, 2014

(54) METHOD OF MAKING SORBENT, THE SORBENT OBTAINED BY THIS METHOD AND THE USES OF THE SORBENT AS FEED ADDITIVE AND MEDICINE

(75) Inventors: Viktoria Alexeevna Lapina, Minsk (BY); Alexander Evgenievich Dontsov, Moscow (RU); Igor Viktorovich Nasonov, Minskaja (BY)

(73) Assignee: Gosudarstvennoe Nauchnoe Uchrezhdenie "Institut Phyziki Im. B.I.: Stepanova" Nacionalnojj Acadzhemii Nauk Belarusi (BY)

(*) Notice: Subject to any disclaimer, the term of this patent is extended or adjusted under 35 U.S.C. 154(b) by 924 days.

(21) Appl. No.: 12/373,407

(22) PCT Filed: Jul. 10, 2007

(86) PCT No.: PCT/BY2007/000001
§ 371 (c)(1),
(2), (4) Date: Apr. 9, 2009

(87) PCT Pub. No.: WO2008/006186
PCT Pub. Date: Jan. 17, 2008

(65) Prior Publication Data
US 2010/0015097 A1   Jan. 21, 2010

(30) Foreign Application Priority Data

Jul. 11, 2006  (BY) ................................. a 20060716
Aug. 11, 2006  (BY) ................................. a 20060837

(51) Int. Cl.
| | | |
|---|---|---|
| *A61K 36/00* | (2006.01) | |
| *A01N 63/00* | (2006.01) | |
| *B01J 20/00* | (2006.01) | |
| *C12N 11/12* | (2006.01) | |
| *A23K 1/00* | (2006.01) | |
| *A61K 33/38* | (2006.01) | |
| *B01J 20/30* | (2006.01) | |
| *B01J 20/24* | (2006.01) | |
| *A61K 36/899* | (2006.01) | |

(52) U.S. Cl.
CPC ............... *A61K 36/899* (2013.01); *B01J 20/30* (2013.01); *B01J 20/24* (2013.01); *A61K 36/00* (2013.01)
USPC .......... 424/776; 424/618; 424/93.4; 502/404; 435/179; 426/615

(58) Field of Classification Search
None
See application file for complete search history.

(56) References Cited

U.S. PATENT DOCUMENTS 4,473,556 A    9/1984  Levanova et al.
6,706,287 B2 *  3/2004  Ranganathan et al. ........ 424/490

FOREIGN PATENT DOCUMENTS

| DE | 2532941 | 2/1977 |
|---|---|---|
| RU | 2060818 | 5/1996 |
| RU | 2067328 | 9/1996 |
| SU | 556811 | 6/1977 |
| WO | WO 9502452 A1 * | 1/1995 |

OTHER PUBLICATIONS

Lapina et al. (2000) Phytosorbent prepared from Sunflower Seed Husks prevents mercuric chloride accumulation in kidney and muscle of adult rabbits. Arch. of Environmental Health, vol. 55, No. 1, pp. 48-50.*
Crini (2005) Prog. Polym. Sci. 30: pp. 38-70.*
Victoria A. Lapina, " Phytosorbent Prepared from Sunflower Seed Husks Prevents Mercuric Chloride Accumulation in Kidney and Muscle of Adult Rabbits", Archives of Environmental Health, Jan./Feb. 2000, vol. 55, No. 1, pp. 48-50.
International Search Report PCT/BY2007/000001; Dated Jan. 11, 2008.

* cited by examiner

*Primary Examiner* — Chris R Tate
*Assistant Examiner* — Russell Fiebig
(74) *Attorney, Agent, or Firm* — Cantor Colburn LLP

(57) ABSTRACT

The present invention relates to a method of making a sorbent, comprising the steeps of crushing seed husks, acid hydrolysis with extraction of water-soluble ballast substances and formation of the target composition of lignin, cellulose and melanin, water rinsing and drying, wherein the acid hydrolysis is made with an 0.1-36% acid solution during 0.3-4.5 hours in the boiling mode under pressure in the range 0.1-0.7 MPa, rinsing is made with water and/or a 0.1-1.0% alkali solution and then softened water, and the product is subsequently dried. The sorbent comprises a porous multilevel matrix on the basis of lignin, cellulose and melanin. The invention further discloses the sorbent and its uses as for prophylaxis and treatment of toxicoses, free-radical pathologies, diarrhea syndromes which are caused by ecotoxicants, viral and bacterial infections, for prophylactic and treatment of animal diseases caused by mycotoxins, pesticides, bad-quality forages in all kinds of animals.

2 Claims, 10 Drawing Sheets

Figure 1:

METHOD OF MAKING SORBENT, THE SORBENT OBTAINED BY THIS METHOD AND THE USES OF THE SORBENT AS FEED ADDITIVE AND MEDICINE

The invention relates to a method of making a sorbent, the sorbent obtained by this method and the uses of the sorbent as feed additive and medicine, in particular, for veterinary use for treatment and for prophylaxis.

There are several known sorbents and methods to make them. The sorbents are either organic and made from wastes of lignocellulosic raw materials of agricultural production: beet-root cake, straw, rice-husk, various wood sawdust, wheat bran, etc or inorganic. The application of these sorption materials for binding and excretion of eco-toxicants such as mycotoxins, heavy metals, organic compounds, etc. from living organisms is known. The known sorbents have, however, several drawbacks.

Inorganic sorbents (clays; aluminum silicates—e.g. Hametox; bentonites; vermiculites etc.) have a narrow spectrum of action, they lower density of animal ration, lead to partial deterioration of gastro-intestinal tract activity because of their versatile chemical structure and the unavoidable presence of harmful impurities, depending on the place of their origin.

An organic sorbent and a method to make it from oil-cake—waste of pumpkin seed processing—is proposed in RU 2 253 510 C1. According to this method, the waste cake is rinsed with water, conditioned for 15-20 minutes, then the water is drained off, fresh water is added again, mixed up, conditioned, the water is drained off again, and the process is repeated until uncolored rinse water is obtained. Then, the residue is dried at the temperature of 100-150° C. up to permanent weight, and then crushed, dispersed, and the grain size 0.2-2.0 mm is selected. The obtained sorbent has a bulk weight of 0.4-0.6 g/cm$^3$, contains at least 4.5 mass percent of nitrogen according to Kjeldahl and at least 4 mass percent of fibre. A disadvantage of the method is a relative complexity of the technology, while the sorbent has limited capability to adsorb pesticides, mycotoxins and similar potentially dangerous and harmful substances.

Furthermore, RU 2 062 647 C1 describes a method and a sorbent made from polysaccharide raw materials. According to this method, polysaccharide raw materials—plant wastes or microorganism biomass (wheat bran, beet-root cake, biomass of *Aspergillus foetidus* M-45, *Trichoderma viride* 13/10 etc.)—are crushed down to the particle size below 3 mm, then a suspension with water/solids of 10-20 (concentration of 5-10%) and pH of 3.5-11.0 is prepared and treated with steam at excessive pressure (above the atmospheric pressure) of 1-1.5 atmospheres for 0.5-4.0 hours. The resulting solid mass is rinsed and dried. The obtained sorbent is used for industrial purification of potable water, for removal of radio-nuclides, heavy metals, and for medical purposes. A disadvantage of the method is a low yield of sorbent, high water consumption and energy demand of the process caused by the need of steam treatment of the initial raw materials. The sorbent obtained by this method has a low sorption capacity and a narrow scope of applications.

A food sorbent and a method to make it from sunflower black seed husks are also known RU 2 255 803 C1. The method comprises removal of ballast substances from sunflower black seed husks by means of solvent extraction at the temperature of 45-55° C. for 30-100 minutes. Extraction gasoline, petroleum-ether and nefras may be used as solvent in the ratio sunflower black seed husks/solvent in the range from 1:5 to 1:20, with subsequent separation of the husks of sunflower black seeds from the solution of ballast substances by settling in the solvent. The separated solid phase of seed husks is diluted with water, the obtained mixture is conditioned for 10-60 minutes and then frozen and conditioned at the temperature of −4° C. to −20° C. for 30-240 minutes with subsequent defrosting at the temperature of 25-100° C. Then, the product is dried at the temperature of 100-200° C., so as to obtain a sorbent for refinement of dark-colored vegetable oil. The disadvantage of the sorbent is its production complexity and limited applications.

Other organic sorbents (cfr. Bio-Mos, Mycosorb, Mycofix Plus), activated charcoal of vegetative origin, etc. are as a rule, expensive and have limited spectrum of action.

Carbon hemosorbent KAU for the treatment of acute poisoning is known from "Carbon hemosorbent KAU". Developer: Institute of sorption and problems of endoecology of Academy of Sciences of Ukraine. 252142, Kiev, Palladin pr., 32/34. Promotional material. 1992. The sorbent is produced on the basis of activated charcoals from crushed pits or nutshells and is characterized by high hydrodynamic and kinetic properties, caused by large volume of macropores, which guarantees adsorption of toxic substances with medium and high molecular weight. The hemosorbent KAU is prescribed as an extracorporal detoxicant of blood of an organism during acute poisoning by industrial and domestic poisons, medicinal preparations, fuligoid toxins, pesticides and some other toxins.

A drawback of the sorbent is low adsorption ability and low selectivity.

A sorbent as described in Patent RU 2 060 818 C1 is effective for refinement of tap water from $Ca^{2+}$ ions. In such a way, if initial content of calcium ions in water was $(21\pm4)\cdot10^{-4}$ m$^{-3}$, then after passing through a column with sorbent, their concentration, measured by Arsenazo III, is $(0.8\pm0.1)\cdot10^{-4}$ m$^{-3}$. The sorbent consists of natural water-insoluble polymer, containing carbon, hydrogen, nitrogen, sulfur and oxygen in specific percentage. The sorbent adsorbs a series of heavy metals and radio-nuclides as well, and effectively works in range pH 2-8.5. The crude oil bound by the sorbent is retained on water surface for a long period of time without need of any surfactants. The sorbent can be used in food industry, in ecology for environment refinement, in particular, for removal of radio-nuclides from solutions, decontamination from petroleum products and in agriculture for excretion of heavy metals from animal's organism. The drawbacks of the obtained sorbent are its limited sorption activity, and also that it contains only one biologically active component—melanin, which substantially limits its practical application.

The method of making the sorbent is from RU 2 060 818 C1 comprises crushing of the hulls (husks) of sunflower black seeds into flour, acid hydrolysis with a hydrochloric acid solution with normality 9-12 for at least 35-45 days at the temperature of 20° C., water rinsing and drying of the hydrolysis products.

Sulfuric acid at concentration 35-50% can be used for hydrolysis. Acidic hydrolysis by sulfuric acid can be carried out at temperature 100° C. during at least 3-6 hours. The crushing is continued until obtaining the flour, which is then treated with 30-50% acid in the weight ratio of 1:8-10. The obtained hydrolysis product is rinsed first with distilled water at standard conditions and then with hot distilled water at 80° C. until no traces of $SO_4^{2-}$ is detected in the running water. Before drying, the product is additionally rinsed with ethanol, dried, and the final phytosorbent is obtained.

A disadvantage of this known method of making the phytosorbent is the low productivity of the process caused by a high consumption of concentrated acid and rinsing water and a high power demand due to a long hydrolysis process. Among the disadvantages of the method are also high concentrations of mineral acids, limited choice of acids, necessity to use the specific hydrolysis regime for each type of acid (this reduce technological effectiveness of the method). The method has also low productivity: 35-45 days at 20° C. or 3-6 hours at 100° C., it requires large amount of distilled water, including hot distilled water, that increase power consumption. Use of spirit for rinsing substantially raise the price of the process and also lead to washing-out of potentially useful biologically active substances. Low output of the final product leads to a non-optimal use of vegetative raw material.

The aim of the invention is to create a method of making an sorbent that does not have the above disadvantages, and an sorbent with a broader application spectrum.

The invention thus proposes a method of the sorbent production comprising the steps of:

crushing of seed husks, acid hydrolysis with extraction of water-soluble ballast substances and formation of target composition of lignin, cellulose and melanin, water rinsing and drying, wherein the acid hydrolysis is made with an 0.1-36% acid solution, preferably between 1 and 36%, more preferably between 1 and 10% and most preferably between 1 and 5% during 0.3-4.5 hours, preferably between 1.5 and 4.5 hours in the boiling mode under pressure in the following range: 0.1-0.7 MPa (1-7 atmosphere) and preferably between the pressure of saturated vapor of the mixture to 3.0 atmospheres, the rinsing is made by water or with a 0.1-1.0% alkali solution and then softened (demineralized) water, and the product is subsequently dried wherein the sorbent comprises a porous multilevel matrix on the basis of lignin, cellulose and melanin having integrated porosity of 0.04 to 50 microns.

The method as claimed has a reduced process cycle due to an optimization of the operation modes and the selection of agents to treat the initial raw materials—seed husks especially sunflower black seed husks, the fruit coat of buckwheat seeds, beans, other colored seed shells, the peels of various berries with dark coloring such as peels of plums, cherries, blueberries, dark grades of grapes, black currant etc.

The basic requirements to the raw material is the presence of the pigment melanin. The sorbent thus obtained has universal sorption properties with respect to broad class of potentially dangerous chemical substances and micro-organisms. For example, it is capable to sorb hazardous chemical substances such as pesticides, mycotoxins, polychlorinated biphenyls, viruses, pathogenic bacteria, and complex hydrocarbons.

The sorbent has a porous multilevel structure with a polymodal pore distribution (micro-, meso- and macro-pores), chemically active centres and biologically active ingredients on the surface, that allows to adsorb molecules of various sizes, geometries and chemical nature.

Sulphuric, hydrochloric, or orthophosphoric acid may be used for acid hydrolysis.

The rinsing of the product may be made with water or a solution of ammonium hydroxide, sodium hydroxide or potassium hydroxide until the pH of the rinsing solution reaches 3.5-4.5.

Prior to rinsing the hydrolysis product with an alkali solution, additional water rinsing may be carried out in the boiling mode for 10-15 minutes.

Rinsing of the neutralized hydrolysis product with softened (demineralized) water is continued until the pH value of the rinsing solution reaches 4.5-6.4. Alternatively, potable water, distillated (condensate) water or de-ionized water may be used for product rinsing.

It has to be noted that the production method generates a sterile product which allows a long shelf live of the sorbent. According to a preferred embodiment, the method further comprises a step of impregnation of the sorbent with silver ions and/or a step of immobilization of microbial biomass of probiotic bacteria.

The sorbent is advantageously impregnated or immobilized directly after its rinsing or after drying.

Impregnation with silver ions is preferably carried out by means of treating the product in static conditions by a water-soluble silver salt, for example, silver nitrate, with the equilibrium concentration of silver ions, and the ion sorption value is defined according Friendlich formula:

$r = K \cdot C^n$, where: r is the sorption value, mmol/g;

K, n (1, 2) are the constants; and

C is the equilibrium concentration, g/l.

Alternatively, the sorbent may be immobilized by means of incubation with a microbial suspension of probiotic bacteria, for example, such as *Bacillus*, or *Lactobacillus*, or *Bifidobacterium* or a mixture thereof with microbial concentration of at least $10^8$ CFU (colony-forming units). The immobilization is carried out according to preferred embodiment at the solid/liquid phase module of 1:10 for at least 1 hour with subsequent extraction and drying of the solid phase. The drying is preferably carried out at the temperature of +37° C. for 24 hours.

According to another aspect of the invention, a sorbent comprising a carbon-containing heteropolymer composition obtained from hydrolysis of seed husks comprising lignin, cellulose, melanin structured into a porous multilevel matrix is proposed.

According to a preferred embodiment, the sorbent comprises

| Lignin | 25-70% w/w |
|---|---|
| Cellulose | 20-65% w/w |
| Melanin | 1-10% w/w., |

According to yet another preferred embodiment, the sorbent comprises:

| Lignin | 39.9-58.8% w/w |
|---|---|
| Cellulose | 40.6-50.9% w/w |
| Melanin | 1.0-8.0% w/w. |

The sorbent may further comprise biologically active carbon-containing substances chosen from the group consisting of: bioflavonoids, polysaccharides (glucose, fructose, saccharose), pectins, leucoanthocyans; catechins, phenol-carboxylic acids, tannins and mixtures thereof.

These products may be present in the sorbent in the following ranges:

bioflavonoids: 142.6-615.5 mg/percent, polysaccharides (glucose, fructose, saccharose): 0.195-0.444%, pectins: 0.499-1.912%, leucoanthocyans: 0.1-2.76%, catechins: 0.2-146.6 mg/percent, phenol-carboxylic acids 212.5-697.9 mg/percent, and tannins: 0.58-0.83%.

wherein 1 mg/percent=10 ppm.

The porous multilevel matrix preferably comprises physically and chemically bonded substructures from lignin particles of band-spiral shape with pore dimensions of 0.1-15 μm, cellulose fibers of lengthwise-stretched shape with pore dimensions of 5-50 μm, and melanin agglomerates sized up to 400 μm from particles of pipe-like shape up to 5 μm long.

The sorbent may further comprise a surface modifier in the form of silver ions or it may comprise a microbial biomass of probiotic bacteria.

Silver ions may be present on the sorbent in the form of actively bonded centres with a strong bond constant in the interval $n_1=(0.013$-$0.019)$ mmol/g for $K=(2.5$-$2.11)\ 10^4\ M^{-1}$ and a weak bond constant in the interval $n_2=(0.064$-$0.074)$ mmol/g for $K=(1.8$-$2.0)\ 10^3\ M^{-1}$.

The microbial biomass of probiotic bacteria preferably contains bacteria of the type *Bacillus Subtilius*, or *Lactobacillus*, or *Bifidobacterium* in the amount of $(0.181$-$2.26)\ 10^9$ CFU/g of sorbent.

According to another aspect, the invention is related to the use of the sorbent as a medicine in particular as a veterinary medicine and is intended for prophylactic and treatment of toxicoses, free-radical pathologies, diarrhea syndromes which are caused by ecotoxicants, viral and bacterial infections, for prophylactic and treatment of animal diseases caused by mycotoxins, pesticides, bad-quality forages (with high peroxide number) in all kinds of animals.

For prophylactic of eco-toxicoses and poisoning by bad-quality forages, the preparation is administered together with fodder in the amount of 0.15-2.0% to the fodder mass depending on the fodder contamination.

For prophylactics and complex medical treatment of infections caused by bacteria of genus *Salmonella, Escherichia, Clostridia, Pasteurella, Campillobacteria, Staphylococci, Streptococci*, viruses of the Newcastle disease, infectious bronchitis, infectious bursal disease (Gumboro disease), enteroviruses and infectious laryngotracheitis, the preparation is administered into the gastrointestinal tract ("the tract") together with fodder in the quantity of 0.2-1.5 g/kg of bodyweight 1-2 times a day during 5-14 days until disappearance of clinical signs of the disease.

Antimicrobial action of the sorbent can be further improved by the introduction of silver by sorption from silver nitride solution with $Ag^+$ concentration $(9.7 \cdot 10^{-4}$-$0.97)$ g/l or by the introduction of probiotic bacteria in not less than $10^8$ CFU/g of the sorbent (CFU—colony-forming unit). Bacteria of the following genus: *Bacillus, Lactobacillus* or *Bifidobacterium* can be used as probiotic bacteria.

The sorbent may also be used to increase the fiber content of feed, as a feed additive, because due to treatment of the raw material, the concentration of vegetative fibers increases up to 98%.

The invention is explained by reference to FIGS. 1-22 wherein.

Figure 2:
Figure 3:
Figure 4:
Figure 5:
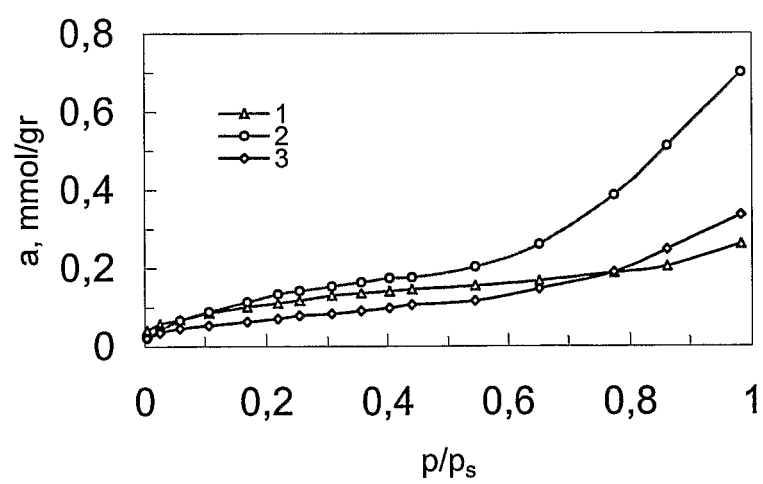
Figure 6:
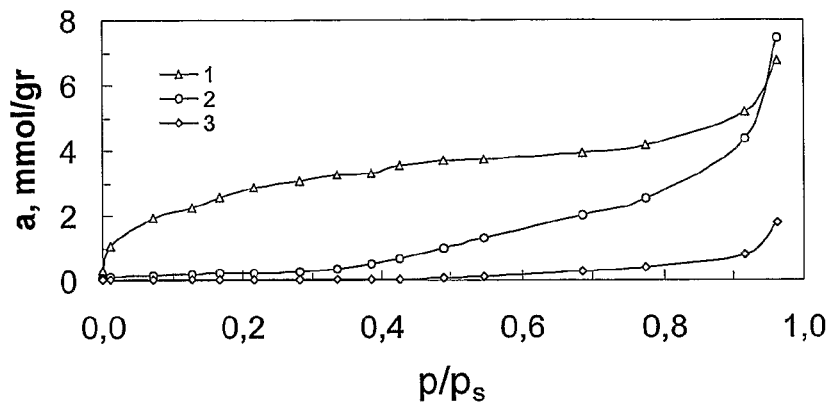
Figure 7:
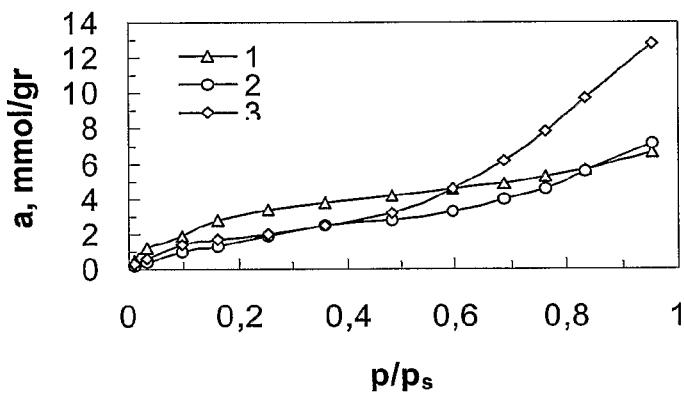
Figure 8:
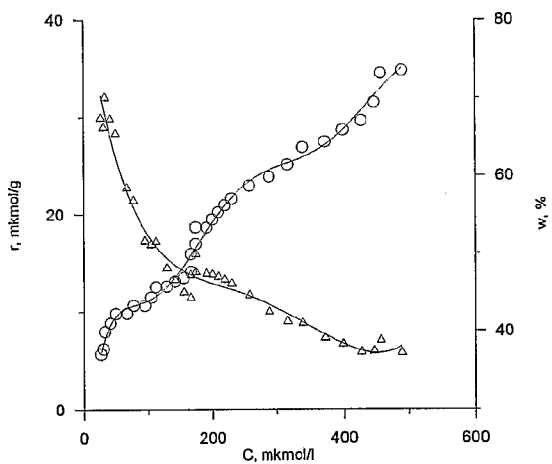
Figure 9:
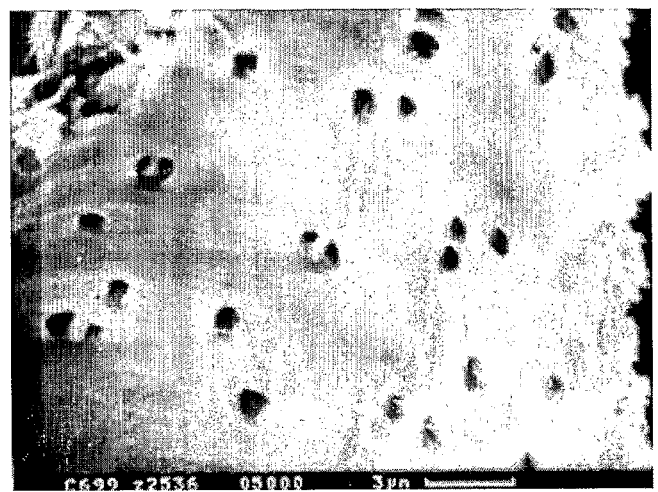
Figure 10:
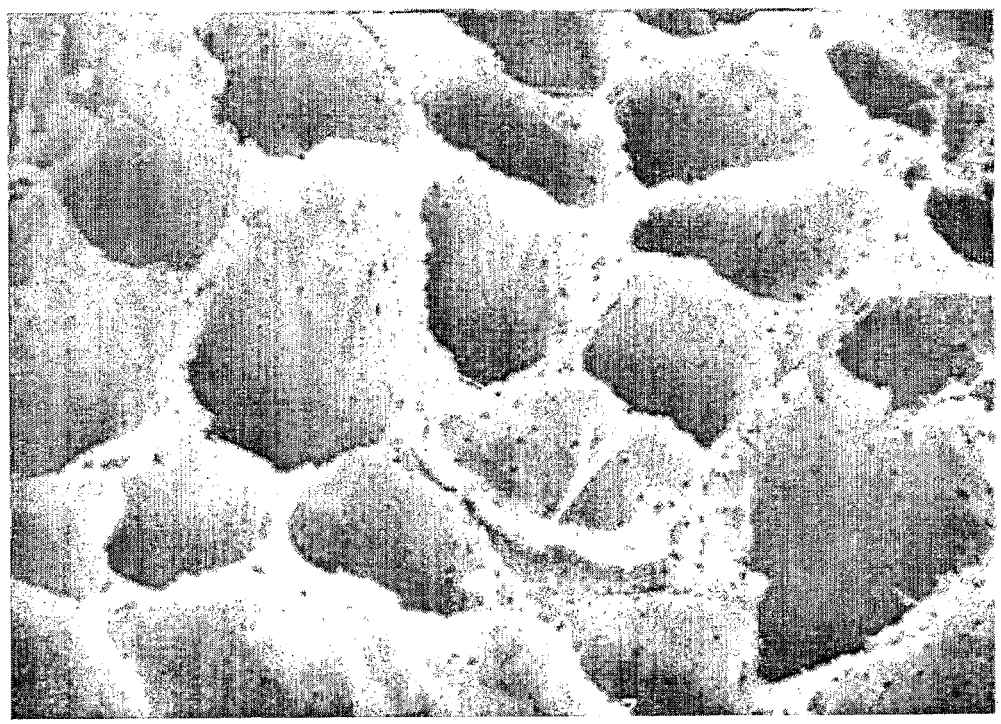
Figure 11:
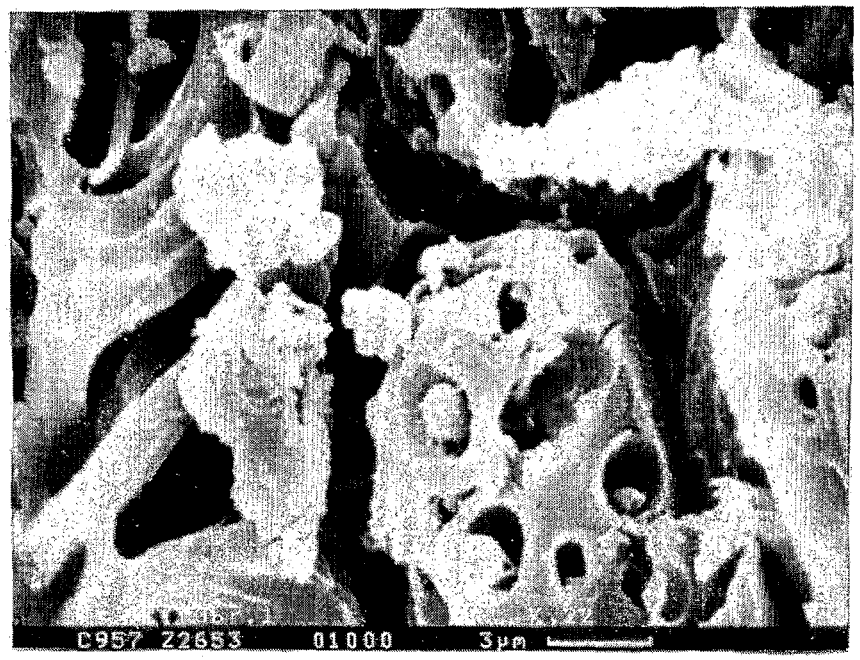
Figure 12:
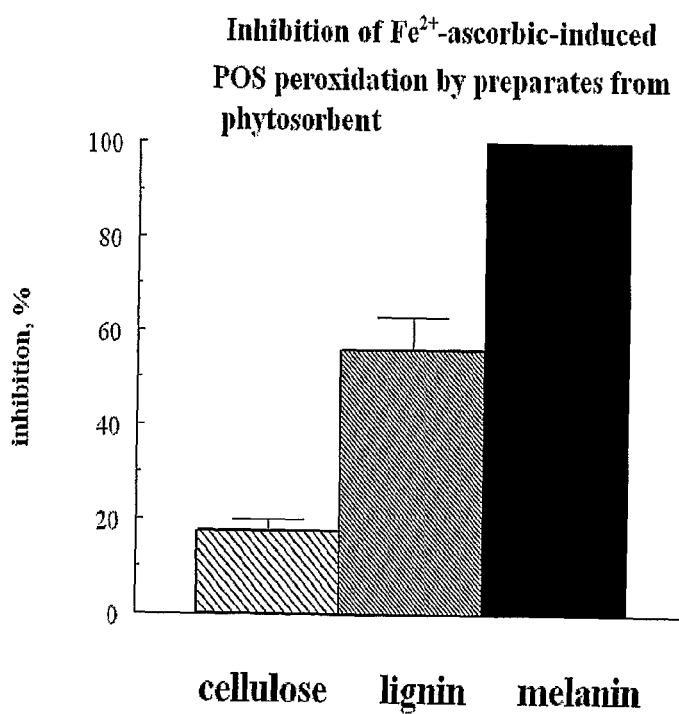
Figure 13:
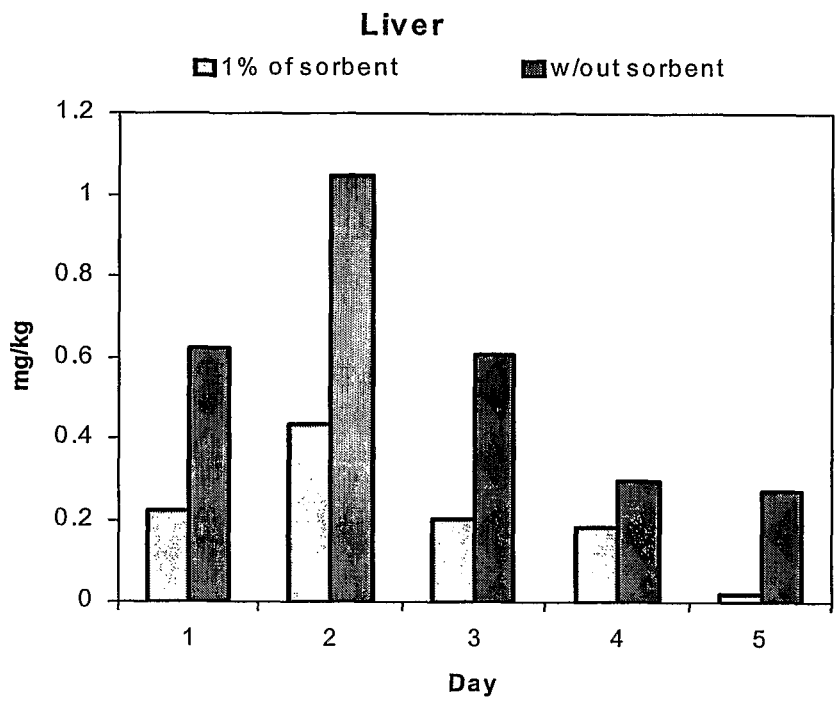
Figure 14:
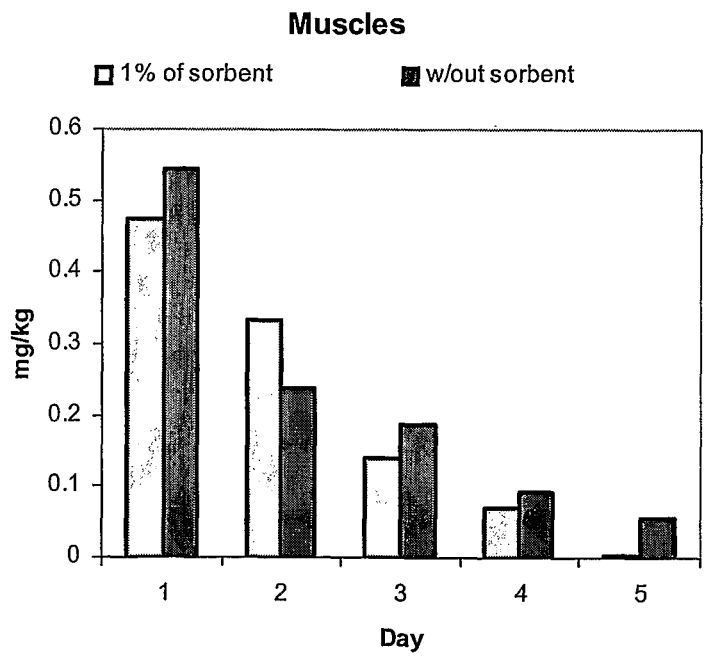
Figure 15:
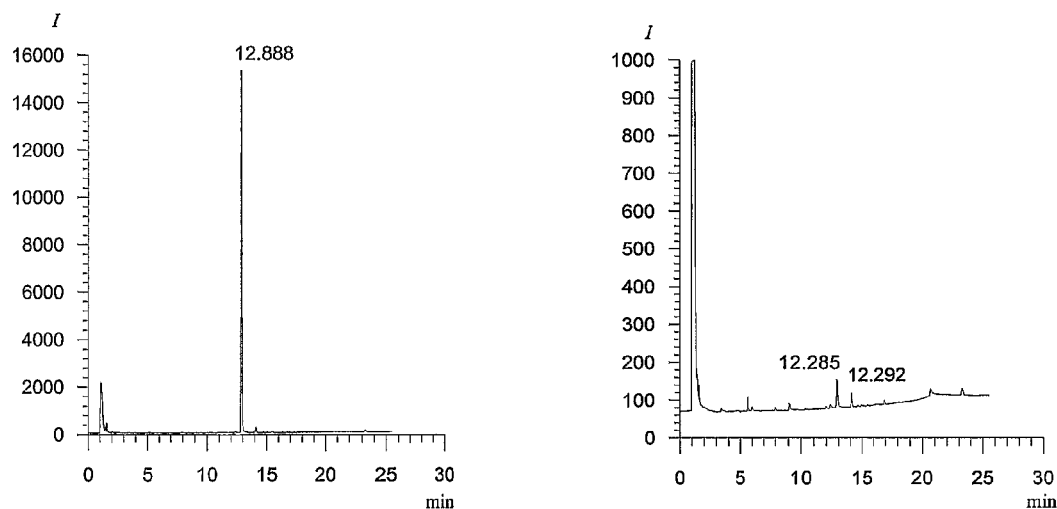
Figure 17:
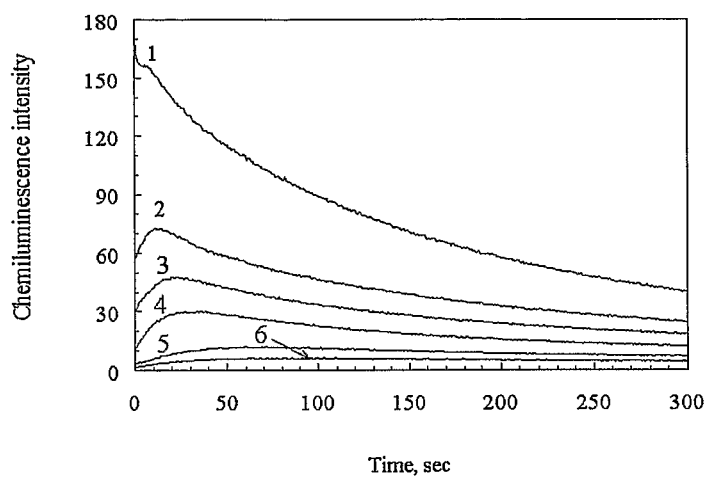
Figure 18:
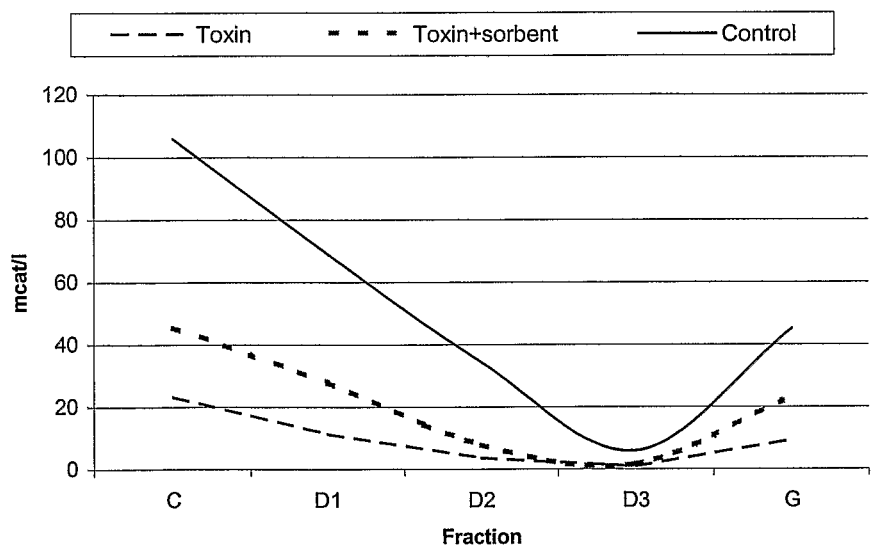
Figure 19:
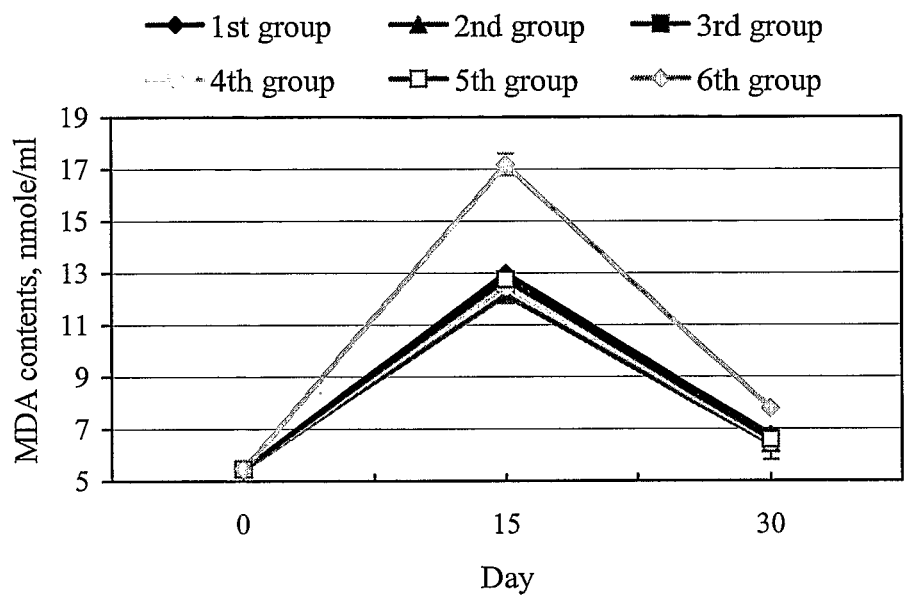
Figure 20:
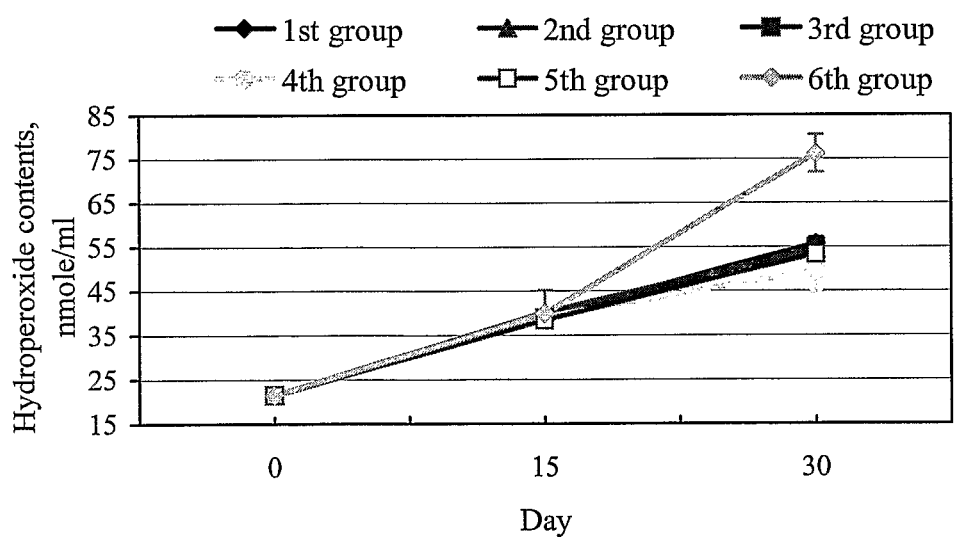
Figure 21:
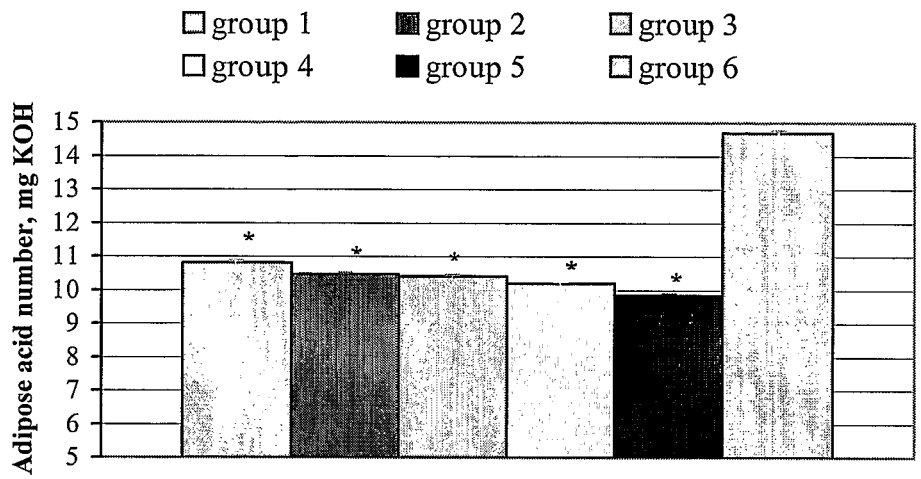
Figure 22:
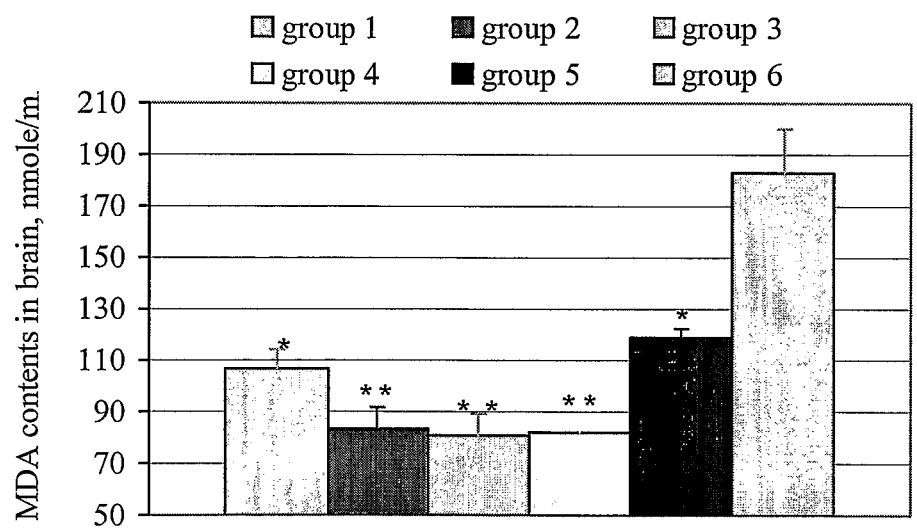

FIG. 1—Photo of the lignin microstructure.
FIG. 2—Photo of the cellulose microstructure.
FIG. 3—Photo of the melanin microstructure.
FIG. 4—Photo of the enterosorbent surface morphology (9000× magnification).
FIGS. 5, 6, 7—Sorption isotherms of benzol, methanol and water by lignin (1), cellulose (2) and melanin (3), respectively.
FIG. 8—Sorption isotherm and silver extraction ratio versus silver concentration, where C is the silver equilibrium concentration (μmol/l), r is silver sorption (μmol/g of sorbent), and w is silver extraction rate (percent).
FIG. 9—Photo of the enterosorbent surface morphology, (5000× magnification).
FIG. 10—Photo of the enterosorbent surface morphology (1000× magnification).
FIG. 11—Photo of the enterosorbent surface morphology modified by the microbial biomass of probiotic bacteria (1000× magnification).
FIG. 12—Comparison chart of the inhibiting activity of the sorbent to peroxidation rate of internal photoreceptor segments, induced by $Fe^{+2}$ ions in the presence of ascorbate.
FIG. 13—Dynamics of residual quantities of lindane in the chicken liver.
FIG. 14—Dynamics of residual quantities of lindane in the chicken muscles.
FIG. 15, 16—Chromatograms of pesticides sorption.
FIG. 17 Quenching of luminol chemiluminescence's by the-sorbent.
FIG. 18—α-amylase activity in mucosa of jejunum.
FIG. 19—Malone dialdehyde contents in serum of chickens.
FIG. 20—Hydroperoxide contents in serum of chickens.
FIG. 21—Acid number of adipose after 30 days of experiment.
FIG. 22—MDA contents in brain after 30 days.

Examples of embodiment of the method of production, the sorbent as well as the uses thereof are given below.

The proposed method of production ensures, at the stage of crushing, destruction of cell shells with formation of microparticles accessible for chemical agents. The hydrolysis of the crushed raw materials is performed by acid agents with concentration of (0.1-36)% (sulphuric, or hydrochloric, or orthophosphoric acid) in the boiling mode under excess pressure (in the range: 0.1-0.7 MPa (1-7 atmospheres)). The hydrolysis process duration is essentially, up to 0.3-4.5 hours, reduced and the consumption of the acid is also decreased. At the same time we observe efficient decomposition of the lignocellulose complex, partial depolymerization of cellulose and formation of strongly acidic, carboxylic, phenolic, carbonylic, hydroxylic and other surface groups in the presence of oxygen. Rinsing of the hydrolysis product with a 0.1-1.0% solution of ammonium hydroxide, or sodium hydroxide, or potassium hydroxide until the pH value of the rinsing solution reaches 3.5-4.5 allows to efficiently neutralize the remaining acid and create an optimum balance of biologically active carbon-containing substances preferably of the following composition: bioflavonoids in the amount of (142.6-615.5) mg percent, polysaccharides (glucose, fructose, saccharose)—(0.195-0.444)%, pectins—(0.499-1.912)%, leucoanthocyans—(0.1-2.76)%, catechins—(0.2-146.6) mg percent, phenol-carboxylic acids—(212.5-697.9) mg percent, and tannins—(0.58-0.83)%. In such alkali rinsing, the subsequent water consumption for rinsing of the hydrolysis product is significantly reduced, and the power consumption of the process as a whole is diminished.

To improve the rinsing efficiency it is possible, prior to treating with alkali solution, to additionally rinse the hydrolysis product with water in the boiling mode for 10-15 minutes, which reduces the alkali consumption on neutralization of remaining acid.

The porous multilevel matrix on the basis of lignin, cellulose and melanin with the integral porosity of 0.04-50 μm is represented at the FIGS. 1-3, 4, 9, and 10. The matrix of the sorbent represents a heteropolymer of irregular structure made of substructures with a broad polymodal pore distribution. The substructures are physically and chemically bonded with each other and formed from lignin particles of the band-spiral shape (FIG. 1) with pore dimensions of 0.04-15 μm, cellulose fibres of lengthwise-stretched shape (FIG. 2) with pore dimensions of 5-50 μm and melanin agglomerates (FIG. 3) with dimension of up to 400 μm from particles in the form of separate pipes up to 5 μm long. The presence of medium and large transport pores and the above characteristics of chemical nature of the heteropolymer matrix internal surface, combined with an optimum balance of biologically active substances and melanin, is believed to ensure both adsorption characteristics (FIGS. 4, 6, and 12) and high antioxidant and antiradical activity of the sorbent, which provides its high medicobiological activity.

A feature of the chemical nature of the heteropolymer matrix internal surface of the sorbent is the presence of protonogenic (carboxylic and hydroxylic) ion-exchange groups, due to which the sorbent acts as a weak-acidic cation exchanger.

Both the heteropolymer chemical components, namely, lignin, cellulose and melanin possessing efficient adsorption and structural characteristics and structured into the porous multilevel matrix, and the presence of chemical groups of acidic character (hydroxylic, carbonylic, carboxylic and others) on the surface of the sorbent, allow to easily modify the sorbent with various metal microelements, for example, silver, or with an antagonistically active biomass of probiotic bacteria.

The sorbent may thus be modified by impregnation with silver ions as described above.

The modification by means of immobilization of antagonistically active biomass of probiotic bacteria is favored by their capability to penetrate into the pores of the sorbent, reproduce inside of it and form conglomerates of probiotics of various shapes and dimensions, depending on the place of their seeding into the structure of the multilevel matrix. Immobilization is made by incubation of the sorbent with a microbial suspension of probiotic bacteria, for example, *Bacillus*, or *Lactobacillus*, or *Bifidobacterium*. After drying to the air-dry condition, the sorbent thus obtained is a complex antibacterial preparation: a heteropolymeric composition with high antagonistic activity to a range of pathogenic microorganisms. An advantage of the sorbent obtained by this method is its high survival ability in the gastrointestinal tract (GIT); it preserves its viability for a long period after drying and ensures a prolonged activity throughout the whole stretch of the GIT.

The Table below presents examples of embodiment of the invention, and results of the study of the obtained sorbent.

EXAMPLE 1

Column 2 of the Table 1

The initial raw material, sunflower black seed husks, is crushed down to 0.5-3.5 mm and treated with a 36% hydrochloric acid solution at solid/liquid module of 1:7 in the boiling mode under pressure of 3 atm for 2.0 hours. Then, the hydrolysis product is rinsed with water with simultaneous boiling for 10 minutes, then, the solid phase is extracted and rinsed with a 1% solution of ammonium hydroxide until reaching the pH value of 4.5, then, the solid phase is extracted again, and its rinsing continues with softened water until obtaining the pH value of 6.2-6.4 in the running water. The obtained product is dried up to the humidity of 22%, and finally sorbent is obtained, which is subject to control tests. The parameters of the obtained sorbent are given in the Table 1 (Column 2).

EXAMPLE 2

Column 3 of the Table 1

The initial material crushed as in Example 1 is treated with a 28% sulphuric acid solution at solid/liquid module of 1:7 for 1.5 hours in the boiling mode under the pressure of 3 atm, rinsed with water with subsequent boiling under pressure for 15 minutes, then, the solid phase is extracted and rinsed with a 0.5% solution of potassium hydroxide until reaching the pH value of 4.0, and the rinsing is continued with softened water until reaching of the pH value of 5.8-6.3 in the running water. The obtained product is dried up to the humidity of 12.5%, and finally the sorbent is subject to control tests. The results of the tests are presented in the Table 1 (Column 3).

EXAMPLE 3

Column 4 of the Table 1

The crushed initial raw material is treated by hydrolysis with a 20% solution of sulphuric acid at solid/liquid module of 1:6 for 1.5 hours at the temperature of boiling under pressure of 2 atmospheres, the solid phase is extracted and rinsed with a 0.1% solution of potassium hydroxide until reaching the pH value of 4.5 with subsequent rinsing with softened water until reaching the pH value of 5.2, dried up to the humidity of 7.8%, and the obtained sorbent is tested. An electronic photo of a typical microstructure of the surface of the multilevel matrix is presented in FIG. 10 (1000× magnification).

EXAMPLE 4

Column 5 of the Table 1

The initial raw material is treated by hydrolysis with a 16% solution of hydrochloric acid at solid/liquid module of 1:7 for 1.5 hours at the temperature of boiling under pressure 1 atmosphere, solid phase is isolated and rinsed with a 1% solution of ammonium hydroxide until reaching the pH value of 3.5 with subsequent rinsing with softened water until reaching the pH value of 4.9. The resulting substance is dried to the humidity of 10.4%, and the obtained sorbent is tested.

EXAMPLE 5

Column 6 of the Table 1

The initial raw material is treated by hydrolysis with a 5% solution of orthophosphoric acid at solid/liquid module of 1:3 for 4.5 hours at the temperature of boiling under pressure 1.5 atmospheres, the solid phase is isolated and rinsed with a 0.1% solution of potassium hydroxide until reaching the pH value of 4.5 with subsequent rinsing with softened water until reaching the pH value of 5.0, dried to the humidity of 8.5%. The obtained sorbent has the parameters presented in the Table 1.

EXAMPLE 6

Column 7 of the Table 1

The initial raw material is treated by hydrolysis with a 0.3% solution of sulphuric acid at solid/liquid module of 1:8 for 4.5 hours at the temperature of boiling under pressure of 2.5 atmospheres, the solid phase is isolated and rinsed with a 0.5% solution of sodium hydroxide until reaching the pH value of 4.2 with subsequent rinsing with softened water until pH of 5.8, dried to the humidity of 0.8%, and, then control tests are conducted. The obtained sorbent has the parameters presented in the Table 1.

EXAMPLE 7

Column 8 of the Table 1

The initial raw material is treated by hydrolysis with a 10% solution of sulphuric acid at solid/liquid module of 1:8 for 0.5 hours at the temperature of boiling under pressure of 2 atmospheres, the solid phase is isolated and rinsed with a 0.1% solution of ammonium hydroxide until reaching the pH value of 4.2 with subsequent rinsing with softened water until reaching the pH value of 5.9, dried to the humidity of 19.8%, and then the control tests are conducted. The obtained sorbent has the parameters presented in the Table. 1.

| | |
|---|---|
| Water content, mass percent | 19.1 |
| Specific capacity, g/l | 240 |
| Acidity of the extract, pH | 2.35 |
| Ash residue, % | 0.6 |
| Sorption capacity by methylene blue (pH 7.0), mg/g | 56.0 |
| Number of silver ions with actively bonded centres with strong bond constant, $n_1$ ($K = 2.5 \cdot 10^{-4} M^{-1}$), mmol/g | 0.013-0.019 |
| Number of silver ions with actively bonded centres with strong bond constant, $n_2$ ($K = 1.8 \cdot 10^{-3} M^{-1}$), mmol/g | 0.064-0.074 |

EXAMPLE 9

Obtaining of the Sorbent Modified with Microbial Biomass of Probiotic Bacteria

The sorbent of Example 4 is heated in the drying cabinet at the temperature of +80° C. for 2 hours. A suspension of

TABLE 1

| | (*)Embodiment Examples of the Invention | | | | | | |
|---|---|---|---|---|---|---|---|
| Indicators 1 | 1 2 M ± m | 2 3 M ± m | 3 4 M ± m | 4 5 M ± m | 5 6 M ± m | 6 7 M ± m | 7 8 M ± m |
| Glucose, % | 0.155 ± 0.003 | 0.185 ± 0.003 | 0.22 ± 0.005 | 0.21 ± 0.007 | 0.205 ± 0.01 | 0.20 ± 0.007 | 0.275 ± 0.003 |
| Fructose, % | 0.085 ± 0.01 | 0.07 ± 0.01 | 0.115 ± 0.003 | 0.084 ± 0.003 | 0.078 ± 0.002 | 0.165 ± 0.003 | 0.165 ± 0.003 |
| Saccharose, % | 0.118 ± 0.002 | 0 | 0 | 0 | 0 | 0 | 0.019 ± 0.0005 |
| Total dissolved sugars, % | 0.36 ± 0.003 | 0.265 ± 0.01 | 0.34 ± 0.003 | 0.293 ± 0.005 | 0.29 ± 0.007 | 0.29 ± 0.005 | 0.44 ± 0.004 |
| Fibre (Cellulose), % | 47.69 ± 0.03 | 46.5 ± 0.35 | 50.45 ± 0.37 | 44.45 ± 0.09 | 50.95 ± 0.1 | 40.5 ± 0.07 | 47.5 ± 0.03 |
| Hydropectin, % | 0.55 ± 0.004 | 0.15 ± 0.001 | 0.12 ± 0.001 | 0.11 ± 0.004 | 0.59 ± 0.009 | 0.65 ± 0.008 | 0.99 ± 0.008 |
| Protopectin, % | 0.44 ± 0.002 | 0.34 ± 0.008 | 0.45 ± 0.001 | 0.38 ± 0.004 | 0.51 ± 0.004 | 1.27 ± 0.009 | 0.51 ± 0.008 |
| Total pectin substances, % | 0.985 ± 0.007 | 0.49 ± 0.004 | 0.57 ± 0.002 | 0.49 ± 0.009 | 1.1 ± 0.0 | 1.91 ± 0.002 | 1.5 ± 0.002 |
| Leucoanthocyans, mg % | 1.67 ± 0.16 | 0 | 0 | 0 | 2.76 ± 0.06 | 1.72 ± 0.14 | 1.62 ± 0.09 |
| Catechins, mg % | 105.0 ± 2.8 | 0 | 146.6 ± 4.15 | 0 | 127.4 ± 3.45 | 104.0 ± 8.67 | 96.2 ± 3.47 |
| Flavonols, mg % | 287.5 ± 1.5 | 343.7 ± 0.02 | 615.45 ± 6.0 | 514.4 ± 1.5 | 226.9 ± 4.5 | 310.0 ± 0.01 | 235.8 ± 0.004 |
| Phenol-carboxylic acids, mg % | 350.84 ± 2.78 | 236.66 ± 3.34 | 697.93 ± 1.95 | 540.0 ± 4.45 | 324.18 ± 2.78 | 299.2 ± 0.56 | 391.68 ± 0.01 |
| Tannins, % | 0.83 ± 0.004 | 0.67 ± 0.007 | 0.77 ± 0.015 | 0.67 ± 0.007 | 0.67 ± 0.01 | 0.58 ± 0.007 | 0.79 ± 0.007 |
| Lignin, % | 46.77 ± 0.33 | 52.8 ± 0.54 | 58.12 ± 0.67 | 51.5 ± 0.63 | 42.35 ± 1.02 | 35.68 ± 0.96 | 39.93 ± 0.084 |

(*)Note: the sorbent composition may vary slightly depending from flower seed varieties, place and climate conditions of cultivation.

EXAMPLE 8

Obtaining of a Silver-Modified Enterosorbent

The sorbent obtained according to any of Examples 1-7 may be impregnated with silver ions in the following manner. The sorbent obtained according to Example 3 in the form of suspension having concentration of 100 g/l and having pH=6.3 is introduced into the $AgNO_3$ solution with silver ion concentration of C=0.057 g/l. Then, the mix is blended and kept for 30-40 minutes in static conditions until the equilibrium concentration is reached. The ion sorption value is set according to the Friendlich formula: $r = K \cdot C^n$, where r is the sorption value, mmol/g; K and $n_{(1,2)}$ are the constants; and C is the concentration of silver ions, $M^{-1}$. Then, the liquid phase is separated by filtration; the solid residue is rinsed with distilled or softened water and dried at the temperature of 100° C. The resulting sorbent has the following characteristics:

probiotic bacteria is prepared, for this purpose a scrap is taken from a daily growth of bacteria *Bacillus Subtilius*, or *Lactobacillus*, or *Bifidobacterium* (of respective strain thereof) into physiological saline and brought by the optical turbidity standard to 100 million ($10^8$) colony-forming units (CFU)/ml. Then, the sorbent is incubated with the obtained microbial suspension for 1 hour at solid/liquid module of 1:10. Under the chosen parameters, 1.0 g of the sorbent contains about $10^9$ CFU of probiotic bacteria, which corresponds to a one-time treatment and prophylaxis dose, provided a 100% sorption thereof from the microbial suspension. Then, the solid phase is separated from the liquid one and dried at the temperature of +37° C. The final sorbent is tested for sorption, and the viability of adsorbed bacteria is controlled by standard methods.

The adsorption and structural properties of enterosorbents obtained according to Examples 3, 8 and 4,9 are presented in Tables 2, 3 respectively.

TABLE 2

| Example | $a_m$, mmol/g | | $Q_1$-$\lambda$, kJ/mol | | A, m²/g | | V, cm³/g | | $V_{mi}$, cm³/g | |
|---|---|---|---|---|---|---|---|---|---|---|
| | $H_2O$ | $C_6H_6$ | $H_2O$ | $C_6H_6$ | $H_2O$ | $C_6H_6$ | $H_2O$ | $C_6H_6$ | $H_2O$ | $C_6H_6$ |
| No. 3 | 1.85 | 0.23 | 5.7 | 5.9 | 117 | 56 | 0.225 | 0.151 | 0.028 | 0.015 |
| No. 8 | 1.98 | 0.23 | 6.5 | 5.1 | 125 | 55 | 0.229 | 0.133 | 0.029 | 0.014 | where: $a_m$, mmol/g, is the monolayer capacity;
$Q_1$-$\lambda$, kJ/mol, is the net adsorption heat;
A, m²/g, is the specific surface;
V, cm³/g, is the total pore volume; and
$V_{mi}$, cm³/g, is the micropore volume.

TABLE 3

| Example | $a_m$, mmol/g | | C | | $Q_1$-$\lambda$, kJ/mol | | A, m²/g | | V, cm³/g | |
|---|---|---|---|---|---|---|---|---|---|---|
| | $H_2O$ | $C_6H_6$ | $H_2O$ | $C_6H_6$ | $H_2O$ | $C_6H_6$ | $H_2O$ | $C_6H_6$ | $H_2O$ | $C_6H_6$ |
| No. 4 | 1.85 | 0.23 | 10 | 11 | 5.7 | 5.9 | 139 | 55 | 0.23 | 0.15 |
| No. 9 | 2.50 | 0.089 | 20 | 51 | 7.3 | 9.6 | 188 | 16 | 0.25 | 0.097 | where C is the constant of the BET equation.

The developed sorbent and its production method have been tested in the conditions of pilot production. The new preparation has proved itself to be an effective curative and prophylactic feed additive to the forages of agricultural animals, and also during acute and chronic intoxication of poultry by pesticides, mycotoxins, poor quality feed and during infection by certain bacteria and viruses.

In vitro and in vivo studies have determined optimal biologically active doses and developed schemes of administration of the sorbent as a pharmaceutical preparation.

Below are examples of the invention implementation.

EXAMPLE 10

Efficiency of Sorption of Mycotoxins, Conditions In Vitro

In the Table 4, the efficiency of binding of various mycotoxins by the sorbent is illustrated as compared with "Mycosorb" a known preparation in veterinary practice (adsorption, % of mycotoxins).

As it seen from the Table 4, sorption activity of the sorbent is higher than that of widely used mycotoxin sorbent, "Mycosorb".

TABLE 4

| | Mycotoxin | | | |
|---|---|---|---|---|
| Sorbent type | Aflatoxin B1 | Zearalenon | Ochratoxin A | T-2 toxin |
| sorbent | 100 (*) | 99.67 ± 0.3 (*) | 77.87 ± 12.3 (**) | 93.6 ± 6.4 (*) |
| sorbent + Ag | 100 (*) | 100 (*) | 64.73 ± 13.3 | 95.45 ± 4.6 (*) |
| Mycosorb | 80.57 ± 8.9 (*) | 76.56 ± 18.2 (*) | 77.31 ± 1.8 (***) | 85.95 ± 14.1 (*) |

Note:
(*) sorption time 15 min;
(**) sorption time 30 min;
(***) sorption time 60 min in conditions of competitive binding.

EXAMPLE 11

Antibacterial Activity of the Sorbent, In Vitro Conditions

TABLE 5

| Sorbent type | Exposition | Staph. aureus strain "Covan I" | E. coli strain "A-M" | Past. multocida strain KMIEV-26 |
|---|---|---|---|---|
| sorbent | 30 min | 99.8 | 21.5 | 9.9 |
| | 24 h | 100.0 | 95.8 | 41.0 |
| sorbent with silver ions | 30 min | 100.0 | 91.9 | 50.2 |
| | 24 h | 100.0 | 100.0 | 100.0 |

As it can be seen from the Table 5, the sorbent with silver ions effectively suppresses the growth of colonies of bacterial cultures of microorganisms *Staph. aureus* strain "Covan I", *E. coli* strain "A-M" and *Past. multocida* strain KMIEV-26 as early as during first 30 min of exposition. This effect is believed to be caused by joint complexing, bio-chemical and catalytic action of enriched biologically active form of the sorbent containing silver on bacterial enzymes, proteins and membrane structures of enteropathogenic microbes.

According to sensitivity to sorbent action, the studied microorganisms are ranked as follows: *Pasteurella multocida, Escherichia coli, Staphylococcus aureus*. In the same time, it is determined that Gram-positive microflora is more sensitive to the sorbent action than Gram-negative.

The sorption capacity of the sorbent with respect to microbial cells as compared to similar products used in veterinary practice is given below.

TABLE 6

| Sorbent | Adsorption of methylene blue, g per 1 g of sorbent | Estimation for microbial cells, millions/g |
|---|---|---|
| sorbent | 0.0226 | 226 |
| sorbent + Ag | 0.0220 | 220 |
| "Mycosorb" | 0.0066 | 66 |
| "Lignasorb" | 0.0103 | 103 |

As it can be seen from the Table 6, sorption capacity of the sorbent with respect to microbial cells is 3.3-3.4 times as large as that for "Mycosorb" and 2.1-2.2 times exceeds that for "Lignasorb" (both are commercial products).

EXAMPLE 12

Antiviral Activity of the Sorbent, In Vitro Conditions

Experimentally established activity of the sorbent with respect to widespread viruses of poultry diseases, the virus of the Newcastle disease (ND), infectious bursal disease (IBD)—Gumboro disease and infectious bronchitis (IB), is presented in Tables 7, 8, 9.

Protective action of the sorbent was detected on various lines of transplantable cell cultures: FL (human amnion), SPEV (kidney of the pig embryo), MDVK (kidney of the bull), FRHK-4 x (kidney of the green marmoset embryo); and also primary-trypsin cell lines: FEK (fibroblasts of the chicken embryo).

Alive dry vaccines against the Newcastle disease (La Sota strain), against infectious bronchitis (strain H-120) and against infectious bursal disease, (strain KMIEV-13), dissolved in normal saline solution, were used as infectious material. Infectious dose of virus is determined by titration of the culture liquid of above mentioned cell cultures.

In Table 7, results of the study of the effect of concentration the sorbent on titers of IBD and IB viruses in cell cultures FL and SPEV are presented.

TABLE 7

| The sorbent concentration, mg/ml | Decrease of IBD virus titer in experiment as compared with control, lg TCD$_{50/ml}$ | | Decrease of IB virus titer in experiment as compared with control, lg TCD$_{50/ml}$ | |
|---|---|---|---|---|
| | FL | SPEV | FL | SPEV |
| 0.325 | 0.75 | 0.5 | 1.0 | 0.75 |
| 0.650 | 1.5 | 1.25 | 1.5 | 1.25 |
| 1.25 | 2.5 | 2.0 | 2.5 | 1.5 |
| 2.5 | 2.75 | 2.25 | 3.25 | 2.75 |
| 5.0 | 3.25 | 3.0 | 3.75 | 3.25 |
| 10.0 | 3.0 | 2.5 | 3.25 | 2.25 |
| 20.0 | 2.75 | 2.5 | 2.0 | 1.75 |

As it can be seen from Table 7, the sorbent effectively protects cell cultures FL and SPEV from development of IBD and IB viruses. Under its action the virus titer is reduced in experiment by 0.5-3.75 lg TCD$_{50/ml}$ (decimal logarithm of tissue cytopathogenic doses in 1 ml) in comparison with the control.

Suppression of infectious activity of IBD and IB viruses by the sorbent depending on time of the sorbent application on SPEV cells monolayer is presented in Table 8.

TABLE 8

| Time of the sorbent application | Sorbent concentration, mg/ml | Virus titer, lg TCD$_{50}$ | Decrease of the virus titer in experiment as compared to control, lg TCD$_{50}$ |
|---|---|---|---|
| 1 hour before infection of cells by IB virus | 5.0 | 0 ± 0.23 | 4.5 |
| 1 hour before infection of cells by IBD virus | 5.0 | 0 ± 0.12 | 3.75 |
| 1 hour after infection of cells by IB virus | 5.0 | 3.0 ± 0.52 | 1.5 |
| 1 hour after infection of cells by IBD virus | 5.0 | 2.5 ± 0.41 | 1.25 |
| Control of IB virus (titer lg TCD$_{50/ml}$) | — | 4.5 ± 0.65 | — |
| Control of IBD virus (titer lg TCD$_{50/ml}$) | — | 3.75 ± 0.37 | — |

As it can be seen from the Table 8, processing of virus suspension by the sorbent results in suppression of infectious activity of IB virus which depends on duration of the processing. Bringing of mixture of the sorbent with virus suspension on cell monolayer after a 30 or 60-minutes exposition leads to complete suppression of infectious activity of IB virus, it was expressed in the absence of CPE (cytopathic effect) in the experiment in comparison with the control. In control, 100% degeneration of cell monolayer was observed.

In Table 9, data on the influence of the sorbent on titer of virus of Newcastle disease of poultry is presented.

TABLE 9

| | sorbent concentration, mg/ml | | | | |
|---|---|---|---|---|---|
| | 0 | 0.325 | 0.65 | 1.25 | 2.5 |
| Titer of NB virus in HAR, log$_2$ | 8.0 | 4.0 | 2.0 | 0 | 0 |

Titer of ND virus without addition of the sorbent is 8.0 log$_2$. After addition of the sorbent in the concentrations of 1.25 and 2.5 mg/ml of virus-containing material the virus is not revealed in HAR (hemagglutination reaction). In the concentrations of 0.325 and 0.65 mg/ml, the presence of virus was marked but in lower titers compared to the control.

Therefore, high protective action of the sorbent is determined in vitro on cell cultures FL and SPEV, infected by virus of infectious bursal disease (Gumboro disease) and virus of infectious bronchitis. The protective action is revealed in reduction of the virus titer by 3.0-3.25 lg TCD$_{50/ml}$ for infectious bursal disease and by 3.25-3.75 lg TCD$_{50/ml}$ for infectious bronchitis as compared with control.

EXAMPLE 13

Antioxidant Activity of the Sorbent, In Vitro Conditions

The antioxidant activity (AOA) of the sorbent (suspension in the phosphate buffer) is studied by the method of luminescence quenching of Luminol. The reaction medium (total volume 3.0 ml) contained 50 mM K-phosphate buffer (pH 7.4), 100 μM EDTA, 2 μM human hemoglobin, 90 μM luminol and various concentrations of the sorbent. In control experiments 0.1 M K-phosphate buffer was used instead of the sorbent. Chemoluminescence was started by addition of the 130 μM hydrogen peroxides into reaction medium. Typical picture of quenching of the luminol chemoluminescence by the sorbent is shown in FIG. 17 (quenching degree for luminol after addition of homogenous sorbent suspension in phosphate buffer in concentrations 170, 250, 410, 810 μg/ml, curves 2—6, respectively, curve 1—control). It can be seen that sorbent reveals AOA, whose efficiency depends on the sorbent concentration.

Calculation of AOA of the sorbent relative to the known antioxidant ascorbate gave the following results: antioxidant activity of the sorbent is 0.04±0.01 mmole of ascorbate per g of dry weight of the sorbent.

EXAMPLE 14

Figure 16:
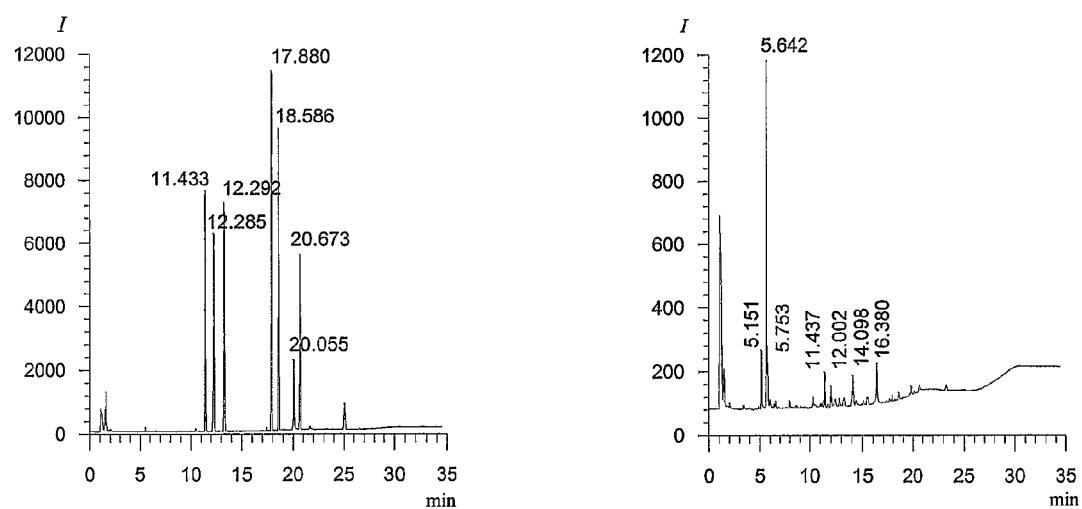

Sorption Activity of the Sorbent Relative to Pesticides, In Vitro Conditions Efficiency of binding of various pesticides by the sorbent in conditions in vitro is illustrated in FIGS. 15,16. In FIG. 15, chromatograms of 2,4-DBE are presented. Before (a) and after (b) adsorption by the sorbent at pH≅7, extract volume 2 ml, pesticide dose 10 μg/g of sorbent. The graph (b) has a scale 1:16. 16Peak at retention time 12.88 min—2,4-DBE. In FIG. 16, chromatograms of pesticide mixture CLP-206 are presented before (a) and after adsorption (b) on the sorbent at pH≈7, extract volume 2 ml, pesticide dose 10 μg/g of sorbent. Scale of graph (b) is 1:10. Peaks at retention time: 1-3 min—impurities in the extragent (hexane); 5-7 min—products of pesticides decomposition; 11.44 min—hexachlor-cyclohexane (lindane); 12.28—heptachlor; 13.29—aldrin; 17.88—dieldrin; 18.59—endrin; 20.05—DDD (product of DDT decomposition); 20.67—DDT.

It can be concluded by this experiment that the sorbent effectively takes up ecologically extremely dangerous pesticides.

EXAMPLE 15

Prophylactic of Mycotoxicoses

Tests were performed on broiler chickens according to the scheme: three groups of chickens (25 birds in each group) were placed in a vivarium under identical conditions of a microclimate. Studies were carried out within 30 days until, poultry become 45 day old. During the whole experiment the chickens of group 1 were receiving grower ration with mycotoxins T-2 in the amount of 100 μg/kg and Ochratoxin A—62 μg/kg of fodder mass. A similar ration was obtained by the chickens of group 2, where the sorbent was added to poisoned fodder in the amount of 1% of fodder mass. The chickens of group 3 received pure grower ration without mycotoxins and sorbent. Peroxide number of fat of all forages corresponded to the norm and did not exceed 0.1% of iodine. The poultry was observed daily for the presence of clinical deviations, every 15 days the weight of chickens was checked and blood samples were taken from axillary vein for definition of hematological and biochemical parameters. After the end of the experiment the poultry was slaughtered, post-mortem examination was carried out with taking of samples of liver and kidneys for toxicological investigations. Heart, liver, spleen, *Fabricius bursa* and proventriculus were also taken for weighing and for histological research. Toxic and biological indices of liver and kidneys of the studied poultry are presented in Table 10.

TABLE 10

| Group | Quantity of probes | Number of infusoria in 1.0 cm$^3$, M ± m × 10$^4$ | Relative biological value, %, M ± m | Toxicity |
|---|---|---|---|---|
| LIVER | | | | |
| 1 | 3 | 309.6 ± 2.25 | 69.9 ± 1.02 | Marked |
| 2 | 3 | 438.1 ± 4.35 | 98.9 ± 0.15 | None |
| 3 | 3 | 443.0 ± 3.46 | 100.0 ± 0.21 | None |
| KIDNEYS | | | | |
| 1 | 3 | 327.4 ± 3.24 | 70.1 ± 0.24 | Marked |
| 2 | 3 | 416.1 ± 2.56 | 89.1 ± 0.35 | Feebly marked |
| 3 | 3 | 467.0 ± 2.26 | 100.0 ± 0.43 | None |

From Table 10 it follows that toxicity of samples of liver and kidneys from the 1st group is well marked, and, respectively, a low biological value of product is observed (69.9% and 70.1%, respectively). In samples of poultry products from the 2nd group, those who received the sorbent, this index is higher (98.9% and 89.1%, respectively) and approaches that of 3rd control group, toxicity in products in 2nd group is absent or feebly marked. Dynamic of the bodyweight changes shows that in the 2nd group of chickens, which received the sorbent, the average daily weight gain is 11.2% higher than in the control 3rd group.

Prophylactic efficiency of the sorbent during mycotoxicosis caused by Zearalenon was determined in analogous manner. Studies were carried on young pigs of initial roaring period.

Three groups of clinically healthy piglets 5 animals in each (age—1.5 month) were formed. Before the experiment, 3 animals from each group were operated for imposition of fistula on jejunum, in order to analyze intestine contents during the process of intestine's digestion under mycotoxicose.

The piglets of the 1st group were fed during 3 weeks by forage poisoned by Zearalenon mycotoxin with the concentration of 0.38-0.40 mg per kg of forage with peroxide number of fat 0.1-0.25% of iodine. The toxicity of forage was checked weekly. The animals of the 2nd group were fed by forage poisoned by Zearalenon mycotoxin with addition of 1.5 g of sorbent per 1 kg of forage. The piglets of the 3rd group served as a control, they were fed by good-quality forage.

Complete clinical investigation of animals was carried out during the whole experiment, at the beginning of the experiment and on the 7th, 14th and 21st day (end of the experiment) blood samples were taken for hematological and biochemical analysis. Blood was sampled from orbital venous sinus. At the beginning of the experiment and on the 21st day the animals were weighed for an average daily weight gain.

Jejunal digestion was studied in parallel, for that the content of jejunum was taken through a fistula by probe. The character of intestinal digestion is judged by activity of an alpha-amylase. Alpha-amylase is determined in a fluid part of intestinal contents, in bioptate on mucous membrane surface, in three desorbing fractions and in a tissue of a mucosa.

On the 21st day experimental pigs were slaughtered with the purpose of morphological and histological research of organs and tissues, veterinary and sanitary inspection of meat and internals.

It was determined, that the consumption of bad-quality fodder with high content of Zearalenon (0.38-0.40 mg/kg of fodder) causes pathological process, characterized by development of an acute inflammation and inflammatory-dystrophic lesion of the liver. Further, this process turns to a chronic course and symptoms of progressive renal insufficiency have appeared. Addition of the sorbent into the forage in an amount of 1.5 g/kg of forage (animals from the 2nd group) results in a marked protective effect, which was revealed in:

decrease of the intensity of the symptoms peculiar to this pathological process, turning of the disease to a chronic form and signs of renal insufficiency are not revealed;
promotion to smaller suppression of small intestine digestion processes, with its subsequent recovering;
improving of the biological value of the meat products: Zearalenon, when entering an organism with fodder, leads to serious dysfunctions of the liver and the kidneys, which influence the relative biological value of these organs. After the addition of the sorbent to forage contaminated by mycotoxins, the biological value of the affected organs was reduced insignificantly in comparison with healthy animals (for high doses of the mycotoxins, that are substantially higher that maximum concentration limit).

Therefore, it was demonstrated that the digestion processes in the jejunum, estimated by α-amylase activity, are reduced and that the sorbent promotes the prevention of the digestion process depression, as it is illustrated in FIG. 18. The functional state of the liver and the kidneys are also significantly affected, but the administration of the sorbent promotes the preservation of their biological value as compared to ill animals.

EXAMPLE 16

Treatment of Diarrhea Syndrome of Poultry 3 groups of 10-days-old chickens (10 heads in each group, 2 experimental and 1 control) were formed to study treatment efficiency. Before the beginning of the experiment chickens of all groups were weighted. During 5 days chickens of the 1st experimental group were fed with mixed fodder with the addition of 1% w/w sorbent-probiotic complex (SPC); chickens of the 2nd group were fed with mixed fodder with the addition of 10 ml (0.02 g) of basic probiotic-analogue "Preparat bacilljarnyj subtilis BPS-44" (Preparation *Bacillus subtilis* BPS-44, Ukraine); chickens of the 3rd group (control) received usual fodder with no addition of medicinal substances. Then the chickens of all groups were weighted and were infected by per os by a suspension of *Escherichia coli* bacteria (pathogenic bird strains SM) 1.2 ml each in the concentration of 250 millions CFU (infectious dose—300 millions CFU). Observation of the infected poultry and administration of preparations under the same scheme was carried out during the next 5 days. Dynamics of the chicken weight gain on different stages of investigation is presented in Table 11.

During the whole period of observation the chickens of the first two groups did not fall ill, were clinically healthy, and consumed actively forage and water. In the control group, depression, appetite loss and decrease of water consumption, 2 chickens with diarrhea and death of 1 chicken on the 4th day after infection were reported. As it seen from Table 11, SPC has an effective growth-stimulating action, exceeding that of the base substance BPS-44. In comparison with the basic substance, the application of the new complex SPC in prophylactic and treatment period increased chickens' weight gain by 2.8-3.4%. In FIG. 11 the surface of the sorbent with microbial biomass is presented (magnification ×1000).

EXAMPLE 17

Study of Treatment and Prophylactic Efficiency of the Sorbent-Probiotic Complex (SPC) in Relation to Diarrhea Syndromes of Piglets For the study of curative and preventive effectiveness of the sorbent-probiotic complex (SPC) during diarrhea syndromes of piglets, seven groups of 1.5-months-age piglets (7 animals in each group) were formed. Diarrhea syndromes were caused by infecting all the experimental piglets by a culture of *Sal. Cholerae Suis* in the dose of $2 \cdot 10^9$ CFU per 1 kg of the animal bodyweight. This culture was selected for the infection of the animals, because *salmonellas* are one of the most dangerous toxic infections, leading to acute food poisoning of humans and to diarrhea syndrome in animals.

After the manifestation and the development of the *salmonellosis* symptoms, the piglets of the 1st group were treated by the antibiotic "Cobactan" intramuscularly in the dose of 0.5 ml per 10 kg of weight and with an antitoxic serum in the dose of 30 ml per animal. Piglets of the 2nd group were treated by the antibiotic "Cobactan" intramuscularly in the dose of 0.5 ml per 10 kg of weight and by the sorbent per os in the dose of 1 g per kg of weight. Animals of the 3rd group were treated by the antibiotic Cobactan intramuscularly in the dose of 0.5 ml per 10 kg of weight and by the SPC per os in the dose of 1 g per kg of weight. Piglets of the 4th group were given the sorbent in the dose of 1 g/kg of weight. The animals of the 5th group received the antibiotic "Cobactan" in the dose of 0.5 ml on 10 kg of piglet weight. The piglets of the 6th group had been administered by the SPC per os in the dose of 1 g/kg of weight. Furthermore, the piglets of 6th group received the sorbent-probiotic complex per os in the dose of 1 g/kg of weight during 5 days before the infection.

The intake of the preparations was carried out once a day during 5 days.

The animals of the 7th group received no treatment and they were the control group.

Full clinical examination of animals was carried out during the whole experiment and blood samples were taken for hematological and biochemical research at the beginning, on

TABLE 11

| Group | Weight, g (background) | On the 5-th day (infection) | | On the 10-th day | |
|---|---|---|---|---|---|
| | | Weight, g | % of weight gain from background | Weight, g | % of weight gain from background/ from infection |
| 1. SPC | 104.0 | 151.9 | 46.1 | 239.8 | 130.6/57.9 |
| 2. BPS-44 | | 148.4 | 42.7 | 236.9 | 127.8/59.6 |
| 3 (control) | | 132.5 | 27.4 | 216.4 | 108.1/63.3 | the 4th and the 10th day (completion of experiment). The piglets were slaughtered on the 10th day of the experiment with the purpose of morphological, histological, bacteriological analysis of the organs and the issues, veterinary and sanitary expertise of meat and internal organs were carried out.

It was determined, that:

the application of "Cobactan" and the antitoxic serum (Group 1), or the application of "Cobactan" and the sorbent (Group 2), or the application of "Cobactan" and the sorbent-probiotic complex (SPC) (Group3) during the treatment of piglets under salmonellosis promote fast (on the 5th day) vanishing of the clinical symptoms of the disease, the suppression of infectious and inflammatory processes, the toxicosis state and the restoring of liver functions.

For the piglets, which were administered the SPC with prophylactic purpose (Group 6), no reliable alterations indicating the development of infectious and inflammatory processes have been recorded during the whole experiment.

Veterinary and sanitary expertise of meat and internals of the carcasses of the animals used in the experiment has shown, that The application of sorbent preparations used in the experiment had no influence on the chemical structure of muscular tissues of the slaughtered animals.

The physical and chemical values of pork of all groups showed no reliable differences and were within the norm. However, the pH index of meat of animals from the 6th group was slightly lower that in the other groups, that helps better maturing and storage of meat.

The Indices of the biological value of the meat of the animals from the experimental and the control groups show no significant differences. There were no manifestations of toxicity in any of the studied samples.

Significant shifts were detected during the definition of the biological value and the food safety of parenchymatous organs of the animals, the liver and the kidneys. Some drop of the biological value of the product was observed in groups 4 and 5. Feebly marked toxicity was also detected in the samples from these groups, which was exhibited in a 10% decrease of the infusorian's reproduction rate, the modification of their form and the presence of dead infusorians.

TABLE 12

| Group of animals | Parameter | | |
| --- | --- | --- | --- |
| | Number of infusoria in $1.0 \text{ cm}^3 \times 10^4$, M ± m | Relative biological value of meat, %, M ± m | Toxicity |
| 1 | 249.0 ± 2.15 | 98.1 ± 1.30 | No |
| 2 | 252.2 ± 3.25 | 98.2 ± 0.25 | No |
| 3 | 257.0 ± 3.42 | 100.0 ± 0.12 | No |
| 4 | 250.2 ± 2.15 | 99.1 ± 2.14 | Weak |
| 5 | 249.3 ± 3.54 | 97.5 ± 1.58 | Weak |
| 6 | 260.0 ± 2.15 | 100.0 ± 0.24 | No |

Alterations of the above stated indices were not observed in the samples from the 1st, 2nd, 3rd and 6th groups. The toxic and biological parameters of the meat are shown in Table 12, and the toxic and the biological parameters, of the liver are shown in Table 13.

TABLE 13

| Group of animals | Parameter | | |
| --- | --- | --- | --- |
| | Number of infusoria in $1.0 \text{ cm}^3 \times 10^4$, M ± m | Relative biological value of %, M ± m | Toxicity |
| 1 | 458.1 ± 2.15 | 98.0 ± 1.25 | No |
| 2 | 438.1 ± 4.35 | 98.9 ± 0.15 | No |
| 3 | 443.0 ± 3.46 | 100.0 ± 0.21 | No |
| 4 | 309.6 ± 2.25 | 89.9 ± 1.02 | Weak |
| 5 | 312.6 ± 4.45 | 86.2 ± 2.42 | Weak |
| 6 | 453.0 ± 4.12 | 100.0 ± 0.51 | No |

EXAMPLE 18

Treatment and prophylactic action of the sorbent during the infection of poultry by viruses of Newcastle disease (NB), infectious laryngotracheitis (ILT) and infectious bronchitis (IB) in vivo.

2 groups of FPF-chickens (free from pathogen factors), 10 birds in each group, age 12 days, were formed for studying of the sorbent influence on the Newcastle disease virus. The chickens from the 1st (experimental) group received the sorbent on the basis of 1% to the forage mass for 5 days before the infection and for 10 days after the infection by the Newcastle disease virus. The chickens from the second (control) group received forage without sorbent. The infection of the chickens of all the groups was carried out by an intramuscular injection of a reference virulent strain "T-53" of the Newcastle disease virus in the dose of 1000 $ELD_{50/ml}$ in 0.2 ml volume. Observations were carried out during 10 days after the infection.

On the 4th day after the infection, illness of 2 chickens was recorded in group 2 (control) with characteristic clinical signs: paralysis of lower extremities, tremor of head. 2 chickens died. On the 5th day, 1 chicken fell ill with characteristic clinical signs in group 1 (experiment), In group 2 (control) 3 chickens fell ill and died. On the 6th day the illness and death of 2 more chickens was recorded in the control group. On the 7th day after the infection, 2 chickens fell ill and died in each group. On the 8th day 1 chicken fell ill and died in the group 1, and 1 (the last) chicken fell ill in the group 2, this chicken died on the 9th day after the infection. In group 1, during further observation for 5 days no falling ill and death was recorded. The data on the sickness and death rate of the chickens is presented in Table 14.

As it is seen, 100% sickness and death rate of chickens is observed in group 2. In the 1st group 60% of chickens did not fall ill.

TABLE 14

| Day (after infection) | Group 1 (experiment) | | Group 2 (control) | |
| --- | --- | --- | --- | --- |
| | Fallen ill | Dead | Fallen ill | Dead |
| 4 | — | — | 2 | 2 |
| 5 | 1 | 1 | 3 | 3 |
| 6 | — | — | 2 | 2 |
| 7 | 2 | 2 | 2 | 2 |
| 8 | 1 | 1 | 1 | — |
| 9 | — | — | — | 1 |
| 10 | — | — | — | — |
| Total | 4 | 4 | 10 | 10 |
| % | 40 | 40 | 100 | 100 |

All the perished chickens were dissected and a postmortem examination was made. A hemorrhagic inflammation of the duodenum with necrotic focuses prominent above the mucosa is recorded for all perished chickens; moreover, for 3, chickens of group 2, hemorrhages in a transition area between the muscle and the glandular ventriculuses were recorded.

2 groups of FPF-chickens, 10 birds in each group, age 12 days, were formed for studying the sorbent influence on the infectious bronchitis virus. The chickens from the 1st (experimental) group obtained the sorbent on the basis of 1% to the forage mass for 5 days before the infection and further for 10 days after the infection by the infectious bronchitis virus. The chickens from the second (control) group obtained forage without any sorbent. The infection of the chickens of the groups was carried out by the intranasal method of a reference virulent strain "Chapaevsky" of the infectious bronchitis virus in the dose of 1000 $ELD_{50/ml}$ in 0.2 ml volume. Observations were carried out for 10 days after the infection. Weighing of the chickens is performed before the experiment (background), after 5 days (infection), and after 15 days (end of experiment).

During the observation period, 5 chickens in the experimental group fell ill, in the control 8 chickens were ill, no loss of chickens was observed. The disease proceeded in a mild form with respiratory syndromes (conjunctivitis, rhinitis). On the 10th day after the infection, the birds of both groups were slaughtered and were subjected to postmortem examination. Serous catarrhal exudate was registered in the trachea of ill birds. The study of the blood serum on the 10th day after the infection by the ELISA (enzyme linked immunosorbent assay) method showed the absence of specific antibodies in 30% of the cases in the experimental group and in 10% of the cases in the control.

The average weight gain 10 days after the infection (see Table 15) was 355.9 g in the experimental group and 302.3 g in the control.

TABLE 15

| Group | Background | After 5 days | After 15 days |
|---|---|---|---|
| 1 (experiment) | 178.2 ± 6.7 | 279.1 ± 9.8 | 635.0 ± 11.3 |
| 2 (control) | 163.7 ± 7.4 | 267.7 ± 8.5 | 570.0 ± 10.4 |

2 groups of FPF-chickens (10 birds in each group, chicken age 25 days) were formed for the study of the sorbent influence on the infectious laringotracheitis virus. The chickens from the 1st (experimental) group received the the sorbent on the basis of 1% of the forage mass for 5 days before the infection and for 10 days after the infection by the infectious laringotracheitis virus. The chickens from group 2 (control) received forage without any sorbent. The infection of the chickens of both groups was carried out by the intratracheal method of a reference virulent strain "Bogatischevsky" of the infectious laringotracheitis virus in the dose of 10000 $EID_{50/ml}$ in 0.2 ml volume. Observations were carried out for 10 days after infection. Weighing of the chickens was performed before the infection, and after 10 days (end of experiment).

During observations, 6 chickens fell ill in the experimental group, in the control group 8 chickens were ill, no loss of chickens was observed. The disease proceeded in a light form with a conjunctive inflammation. On the 10th day after the infection, the birds of both groups were slaughtered and were subjected to postmortem examination. Fibrinous conjunctive inflammation was registered in the ill birds. The study of the blood serum on the 10th day after infection by the ELISA method showed the absence of specific antibodies in 20% of cases in the experimental group and in 10% cases in the control.

TABLE 16

| Group | Background (infection) | After 10 days |
|---|---|---|
| 1 (experimental) | 734.4 ± 11.0 | 1520 ± 12.3 |
| 2 (control) | 715.6 ± 9.9 | 1480 ± 12.8 |

The average weight gain 10 days after the infection (see Table 16) was 785.6 g in the experimental group and 764.4 g in the control.

Therefore, the high curative and prophylactic efficiency of the sorbent is revealed during infection of chickens by the Newcastle disease virus: prevention in experiment is 60%, in the control—0%. The high efficiency of the sorbent with respect to the given virus is associated with its basic localization in small and large intestines.

A lower efficiency of the sorbent was recorded during the infection of chickens by viruses of infectious bronchitis and infectious laryngotracheitis, it is obviously related to main localization of these viruses in respiratory organs.

EXAMPLE 19

Treatment of Piglets Under Toxic Hepatodystrophy

The treatment was performed on two groups of piglets under toxic hepatodystrophy, 15 animals in each group. The piglets of the first (experimental) group were administered sorbent as a main curative and prophylactic substance, together with fodder in the dose of 0.5 g per kg of piglet bodyweight daily until recovery. Animals from the second (control) group were in the same conditions of feeding and keeping as the experimental, and the treatment was performed by a standard substance: Geomicine antibiotic.

During the treatment, the clinical status of all the animals was being determined. On the first, 3, 6, and 9th day of treatment, blood of 5 piglets from each group was sampled for biochemical analysis. Dynamics of some indices of fat, pigment and protein exchange under the the influence of the treatment is presented in Table 17 (M±m, P).

As it can be seen from the results, the recovery of the antitoxic function of liver, the optimization of fat and pigment exchange of the animals of the experimental group take place as early as on the 3rd day of treatment, and even more so on the 9th day. After the treatment by the substance, the processes of reparative regeneration of the liver structures are recorded, this is revealed in a decrease of the number of focuses of hepatocyte necrobiosis, and in a decrease of the liver girder destruction and in an insignificant quantity of proliferates.

TABLE 17

| Index | Group of piglets | Before treatment | Day of treatment 3 | 6 | 9 |
|---|---|---|---|---|---|
| Cholesterol, mmole/l | Experimental | 4.5 ± 0.03 | 3.2 ± 0.02 | 2.3 ± 0.07 | 2.2 ± 0.05* |
|  | Control | 4.6 ± 0.04 | 4.5 ± 0.03 | 4.0 ± 0.01 | 3.4 ± 0.05** |
| Bilirubin, μmole/l | Experimental | 6.36 ± 0.12 | 5.25 ± 0.10 | 4.53 ± 0.05 | 2.81 ± 0.052* |
|  | Control | 6.0 ± 0.06 | 6.1 ± 0.063 | 5.60 ± 0.05 | 4.43 ± 0.070 |
| Total lipids, mole/l | Experimental | 3.7 ± 0.08 | 3.3 ± 0.01 | 2.9 ± 0.07 | 2.6 ± 0.03* |
|  | Control | 3.6 ± 0.06 | 3.5 ± 0.01 | 3.6 ± 0.04 | 3.6 ± 0.03 |
| Lypoproteids, g/l | Experimental | 1.2 ± 0.03 | 0.8 ± 0.06 | 0.7 ± 0.02 | 0.7 ± 0.03* |
|  | Control | 1.2 ± 0.03 | 1.1 ± 0.05 | 1.0 ± 0.02 | 1.1 ± 0.04 |
| Albumines, g/l | Experimental | 21.8 ± 0.49 | 22.3 ± 0.51 | 23.2 ± 0.17 | 24.8 ± 0.02** |
|  | Control | 20.9 ± 0.82 | 21.4 ± 0.67 | 21.5 ± 0.63 | 21.9 ± 0.49 |
| Total protein, g/l | Experimental | 64.8 ± 0.27 | 63.2 ± 0.10 | 59.5 ± 0.33 | 56.7 ± 0.25** |
|  | Control | 64.9 ± 0.08 | 65.1 ± 0.10 | 64.9 ± 0.10 | 64.8 ± 0.10 |
| Glucose, mmole/l | Experimental | 4.0 ± 0.07 | 3.7 ± 0.02 | 3.3 ± 0.01 | 3.3 ± 0.02* |
|  | Control | 4.1 ± 0.09 | 4.0 ± 0.03 | 3.7 ± 0.03 | 3.5 ± 0.03** |

Note:
*$P < 0.001$ as compared with animals before treatment;
**$P < 0.01$ as compared with animals before treatment.

EXAMPLE 20

Influence of the sorbent on the antioxidant protection system of the organism of broiler chicken during feeding by forage with high content of peroxided lipids (POL) 6 groups of 15-days-old broilers were formed for the tests. The test duration was 30 days. Soybean oil was added to the fodder in an amount of 4 ml per 100 g of fodder (acid number of fodder is between 26 and 30.0 mg KOH, peroxide number between 0.45% and 0.59% iodine during the entire, test period; (the norm being not more than 20.0 mg KOH and not more than 0.3% of iodine). Chickens of the 1st, 2nd, 3rd and 4th groups were given fodder with spoilt fat. The sorbent was mixed with the fodder in the quantity of 0.5% to fodder mass in the first group, second—1%, 3rd—1.5%, 4th—2%. The fifth group of chickens was fed by usual fodder for broilers (receipt 5B) with normal peroxide and acid numbers of fat (acid number of fat is 20.0 mg KOH, peroxide number of fat is 0.06% of iodine). The sixth group of chickens was given analogous fodder with soybean oil addition with peroxide parameters as in the 1st-4th groups.

Everyday, observations were carried out in all the groups of birds during the experiment. The clinical state of the poultry, its behavior and its consumption of fodder were taken into account. Weighing of the poultry and blood sampling (whole and for serum) were performed before the start of the experiment (background), and on the 15th and 30th day of the experiment. Blood tests included the determination of the indices of peroxide oxidation of lipids (POL)—malone dialdehyde (MDA), lipid hydroperoxides, superoxiddismutase (SOD) activity.

At the end of the experiment, the chickens were slaughtered and samples of internal fat and brain were taken. Acid and peroxide numbers of the internal fat were determined. Concentration of MDA in the brain was determined.

Significantly lower SOD activity is observed on the 30th day of experiment in groups 2-4 of chickens as compared with group 6 but not exceeding that of group 5 (fodder with normal fat). It is an evidence of reducing of POL processes in test groups as compared with the control. Protective action of the sorbent is confirmed also by a significant decrease of hydroperoxides in the test groups on the 30th day of the test, and malone dialdehyde concentration on the 15th and 30th day of the experiment.

The study of the other biochemical and hematological parameters showed that the sorbent has a highly pronounced protective effect from negative action of fodder with increased content of peroxide oxidation products in conditions in vivo. Indeed, MDA concentration in blood of chickens from the experimental groups was 16-18% lower, SOD activity was 10-12.5% lower, hydroperoxide content—28-35% lower as compared with chickens that were given oxidized fodder without any sorbent. These values in the test groups are close to that of the chickens from the group with normal fodder. Acid number of the internal fat of chickens that were given sorbent in different doses was 26-30% lower and does not differ significantly from that of the chickens with normal fodder. MDA concentration in brain of chickens of the test groups was by 42-56% lower as compared to the chickens that were given oxidized fodder without any sorbent, that is illustrated by FIGS. 19, 20, 21, 22, 7, 8, 9, 10.

Thus, the application of the sorbent has a normalizing impact on the main parameters of peroxide oxidation of lipids. Preparation should be administered during the whole period of feeding by fodder with high lipid oxidation degree.

EXAMPLE 21

Treatment of Animals by the Sorbent during Acute and Chronic Poisoning by Pesticides Tests during acute poisoning by herbicide 2,4-D and by insecticide—Lindane (1,2,3,4,5,6-hexachlor-cyclohexane) were carried out in the following way: Two batches of 2 groups of 30-days-old broiler chickens (25 birds in each group) were formed. In each batch, one group of chickens received the sorbent with the forage, 1% to forage mass. The second group received forage without any sorbent. On the second day after the start of the experiment, chickens were poisoned by a single intake into the crop with the help of probe of 2,4-D (in the first batch) in a dose of 500 mg/kg of bodyweight, and in the second batch by Lindane in a dose of 15 mg/kg of bodyweight. Observations of all poultry were performed daily taking into account the clinical state. On the 1st, 2nd, 3rd, 4th, 5th day after administration of the pesticide, 5 chickens from each group were slaughtered with subsequent sampling of muscles and liver tissue for the definition of the residual amounts of pesticides.

The dynamics of the residual amounts of herbicide 2,4-D and Lindane are presented on diagrams (FIGS. 13, 14) and illustrate the efficiency of the sorbent application during acute poisoning of poultry by pesticides. From the chickens' liver, herbicide 2,4-D is removed almost completely on the 4th day, Lindane—on the 5th day, at the same time, smoother clinical signs of poisoning are recorded as compared with the control groups of poultry, which didn't receive the sorbent.

The efficiency of the sorbent application during chronic poisoning by herbicide 2,4-D and Lindane is illustrated in Tables 18 and 19, respectively, where the dynamics of bodyweight of chickens, which received the sorbent, is shown.

Two batches of 4 groups of 30-day broilers, 25 birds in each group, were formed for experiment. In the first batch, chickens of 1, 2, 3 groups were injected with herbicide 2,4-D in the dose of 200 mg/kg of bodyweight. In the second batch, insecticide Lindane was administered into the crop with the help of probe in the dose of 5 mg/kg of bodyweight daily during 20 days. The forth group serves as the control in both batches. The first group of chickens, in each batch, received the sorbent in the amount of 1% to fodder mass. The second group received the phytosorbent with fodder in the amount of 2%. The third and fourth groups, were kept on usual ration without sorbent. Observation over poultry in all groups of both batches was performed daily, taking into account its clinical state. Definition of bodyweight, sampling of blood for biochemical and hematological research were carried out in the following terms: background, 10, and 20 days.

TABLE 18

| | Chicken bodyweight, g | | | Average daily weight |
|---|---|---|---|---|
| Group | Background | 10 days | 20 days | gain, g |
| 1 (1% of sorbent) | 1120 ± 16.0 | 1525 ± 21.0 | 1696 ± 20.0 | 28.8 |
| 2 (2% of sorbent) | 1110 ± 14.0 | 1640 ± 19.5 | 1745 ± 21.0 | 31.75 |
| 3 (w/out sorbent) | 1100 ± 15.0 | 1325 ± 16.8* | 1446 ± 18.2* | 17.3* |
| 4 (control) | 1100 ± 14.0 | 1520 ± 22.0 | 1650 ± 17.5 | 27.5 |

TABLE 19

| | Chicken bodyweight, g | | | Average daily weight |
|---|---|---|---|---|
| Group | Background | 10 days | 20 days | gain, g |
| 1 (1% of sorbent) | 808 ± 12.0 | 1157 ± 20.0 | 1395 ± 20.0 | 29.3 |
| 2 (2% of sorbent) | 764 ± 10.0 | 1120 ± 14.5 | 1425 ± 23.0 | 33.05 |
| 3 (w/out sorbent) | 788 ± 15.0 | 1032 ± 18.5* | 1270 ± 15.4* | 25.4* |
| 4 (control) | 762 ± 11.0 | 1138 ± 20.0 | 1390 ± 17.5 | 31.4 |

*reliable difference with group 4 ($P < 0.01$)

No significant differences were reported in weight gain dynamics, hematological and biochemical parameters of the chickens, which received the sorbent in 1% and 2% of the fodder mass, during chronic poisoning by pesticides in comparison with control chickens kept on usual ration. The growth and development of chickens which were not administered the sorbent, during chronic poisoning by pesticides were retarded in comparison with chickens of control groups. Deviations in some hematological and biochemical parameters from chickens of control group were also recorded. It thus shown, that the administration of the sorbent promotes fast removal of pesticides during acute poisoning, and normalizes clinical state and exchange processes during chronic poisoning.

EXAMPLE 22

Influence of the Sorbent on Productivity of Hens during their Keeping and on Quality of Poultry Farming Products The Influence of the sorbent on egg quality was studied on 4 groups of layer hens, 25 birds in each group (age—160 days, breed Hisex white). The duration of the experiment was 30 days. The first group of poultry was kept on standard, good-quality mixed fodder, PK 1B. The second group received similar mixed fodder with the addition of oxidized soybean oil at the rate of 1% to forage mass, fat peroxide value of forage was within 0.4-0.5% of iodine. The third group of poultry received mixed fodder with oxidized soybean oil, as in the 2nd group, but with additional intake of the sorbent, 1% to forage weight. The fourth group—control-received mixed fodder PK 1B with addition of good-quality soybean oil, 2% to forage weight. During the test, the egg-laying qualities of hens were recorded daily with the determination of the acid number of egg yolk, the content of vitamin A and carotinoids; as well as morphological parameters (index-form, weight, shell thickness etc.). The presence of antibodies to the virus of Newcastle disease in HAIR (hemagglutination-inhibition reaction) and to infectious bursal disease in DPR (diffusive precipitation reaction) was determined in the egg yolk. The poultry were vaccinated against these diseases at 120-days age.

Parameters, illustrating the influence of the sorbent on egg-laying quality, the dynamics of acid number of the yolk, the egg quality according to standard indices and the level of transovarial antibodies in the egg yolk are presented in Tables 20, 21, 22, 23.

According to Table 20, the greatest egg-laying ability was observed in the 3rd group, where hens received substandard forage with the sorbent and in group 4, where fodder with addition of good-quality oil was used. The lowest egg-laying quality was recorded in group 2, where poultry received bad-quality fodder without the sorbent.

TABLE 20

| Group of poultry | Number of eggs for different periods | | | Eggs during experiment, total | Number of eggs on 1 hen |
|---|---|---|---|---|---|
| | 1-10 day | 11-20 day | 21-30 day | | |
| 1 | 200 | 220 | 227 | 647 | 25.9 |
| 2 | 200 | 225 | 212 | 636 | 25.5 |
| 3 | 212 | 241 | 220 | 674 | 27.0 |
| 4 | 209 | 238 | 223 | 670 | 26.8 |

TABLE 21

| | Acid number of egg yolk (mg KOH) during experiment | | |
|---|---|---|---|
| Group of poultry | 1 decade | 2 decade | 3 decade |
| 1 | 6.45 ± 0.3 | 7.10 ± 0.4 | 7.58 ± 0.3 |
| 2 | 6.84 ± 0.3 | 7.60 ± 0.3 | 7.72 ± 0.4 |
| 3 | 6.03 ± 0.4* | 5.90 ± 0.3* | 6.40 ± 0.4* |
| 4 | 6.40 ± 0.3 | 6.80 ± 0.2 | 7.60 ± 0.4 |

*Reliable differences at $P < 0.05$

TABLE 22

| Group | Vitamin A, μg/g | Index-form | Hau units | Carotinoids, μg/g | Shell thickness, mm | Egg weight, g | White height, mm |
|---|---|---|---|---|---|---|---|
| 1 | 7.75 ± 0.3 | 76.9 ± 2.1 | 84.0 ± 3.0 | 18.29 ± 1.1 | 0.36 ± 0.01 | 53.4 ± 2.3 | 7.09 ± 0.4 |
| 2 | 7.79 ± 0.3 | 75.0 ± 2.0 | 81.75 ± 3.0 | 16.08 ± 1.3 | 0.32 ± .02 | 53.6 ± 2.1 | 6.43 ± 0.2 |
| 3 | 8.15 ± 0.4* | 76.6 ± 2.3 | 84.4 ± 2.5 | 19.58 ± 1.0* | 0.34 ± 0.01 | 61.4 ± 2.0* | 6.6 ± 0.4 |
| 4 | 7.92 ± 0.3 | 76.2 ± 2.3 | 81.9 ± 2.6 | 18.5 ± 1.1 | 0.36 ± 0.02 | 55.1 ± 2.2 | 6.49 ± 0.3 |
| Norm: | Not < 6.0 | 70-80 | Not < 78 | Not < 15.0 | Not < 0.34 | 52-67 | 6-8 |

*$P < 0.05$

According to Table 21, the acid number of egg yolk, obtained from poultry of group 3 was significantly less than that in the 2nd group; it confirms the positive influence of the sorbent on this parameter of egg quality during intake of low-quality forage, with a high degree of fat oxidation.

According to table 22, parameters of the egg quality from all groups of poultry were within the norm. However, key parameters such as vitamin A content, carotinoids content and average weight of eggs were significantly higher in the 3rd group. The greatest difference was recorded in comparison with the 2nd group: vitamin A content—by 4.6%, carotinoids—by 21.8%, average weight—by 1.6%.

According to Table 23, titers of transovarial antibodies to ND and IBD (Gumboro disease) viruses in egg yolks, produced from poultry with poor-quality mixed fodder (group 2) were much lower than those in other groups.

TABLE 23

| Group | Titers of antibodies, $\log_2$ | |
|---|---|---|
| | to ND virus | to IBD virus |
| 1 | 4.1 ± 0.2 | 1.8 ± 0.1 |
| 2 | 2.6 ± 0.1* | 0* |
| 3 | 4.0 ± 0.2 | 1.6 ± 0.1 |
| 4 | 3.8 ± 0.1 | 2.0 ± 0.1 |

*$P < 0.05$

Therefore, the addition of the sorbent to the basic ration of layer hens (1% of forage weight) normalizes the egg-laying ability and the quality parameters of the eggs, which are affected by bad quality of fodder, at the same time, the sorbent normalizes transovarial immune response.

The sorbent has passed the necessary test cycle for prophylactic and treatment of animal diseases and can be recommended for broad use in the pharmaceutical market for animal and poultry farming. Its use is especially efficient as prophylactic substance in full-ration combined fodder for elimination of negative influence of ecotoxicants on animals' organism in areas of constant or temporary technogenic contamination and in epizooty areas for prophylactic of diseases and toxic states of animals, for reduction or elimination of the necessity to use antibiotics or other unsafe antidote substances.

An essential advantage of the new preparation is its high manufacturability and efficiency of use, broad spectrum of action, and cheapness as compared with existing analogues.

The invention claimed is:

1. A method of making a phytosorbent, comprising:
   a) crushing seed husks that contain lignin, cellulose, melanin, and at least one biologically active carbon-containing substance;
   b) hydrolyzing the crushed seed husks with an 0.1-36% acid solution for 0.3-4.5 hours at boiling temperature and under pressure in the range of 0.1-0.7 MPa, thereby obtaining a hydrolysis product comprising a solid phase and a liquid phase;
   c) extracting the solid phase of the hydrolysis product, thereby obtaining a solid product;
   d) rinsing the solid product obtained in step (c) with boiling water;
   e) rinsing the solid product obtained in step (d) with 0.1-1.0% alkali solution;
   f) rinsing the solid product obtained in step (e) with softened water;
   g) drying the solid product obtained in step (f);
   h) impregnating the solid product obtained in step (g) with silver ions, wherein impregnation is carried out by blending the dried product of step (g) with a silver salt solution, and keeping the blend under static conditions until an equilibrium concentration of silver ions is reached, wherein the ion sorption value is set under Friendlich formula:

$r = K \cdot C^n$, where r is the sorption value, mmol/g;
   K, n are the constants; and
   C is the equilibrium concentration, g/l.

2. The method according to claim 1, wherein the at least one biologically active carbon-containing substance is selected from the group consisting of: bioflavonoids, polysaccharides, pectins, leucoanthocyans, catechins, phenol-carboxylic acids, tannins and mixtures thereof.

* * * * *